(12) United States Patent
Dunsmore et al.

(10) Patent No.: US 8,931,478 B2
(45) Date of Patent: Jan. 13, 2015

(54) PATIENT INTERFACE ASSEMBLY FOR RESPIRATORY THERAPY

(75) Inventors: Thomas J Dunsmore, Glendora, CA (US); Geoffrey C. Wise, Benicia, CA (US); Thomas C. Wilschke, Chicago, IL (US); Louis P. Mingione, Chicago, IL (US)

(73) Assignee: Carefusion 2200, Inc., San Diego, CA (US)

( * ) Notice: Subject to any disclaimer, the term of this patent is extended or adjusted under 35 U.S.C. 154(b) by 1465 days.

(21) Appl. No.: 12/274,083

(22) Filed: Nov. 19, 2008

(65) Prior Publication Data

US 2009/0126731 A1 May 21, 2009

Related U.S. Application Data

(60) Provisional application No. 60/988,977, filed on Nov. 19, 2007.

(51) Int. Cl.
*A61M 15/00* (2006.01)
*A61M 16/10* (2006.01)
*A62B 9/00* (2006.01)
*A62B 9/02* (2006.01)
*A61M 16/14* (2006.01)
(Continued)

(52) U.S. Cl.
CPC ........... *A61M 16/14* (2013.01); *A61M 16/0051* (2013.01); *A61M 16/08* (2013.01); *A61M 16/127* (2013.01); *A61M 11/06* (2013.01); *A61M 16/0096* (2013.01); *A61M 16/0816* (2013.01); *A61M 16/12* (2013.01); *A61M 2016/0027* (2013.01); *A61M 2202/0208* (2013.01); *A61M 2202/0468* (2013.01); *A61M 2205/332* (2013.01); *A61M 2205/502* (2013.01); *A61M 2205/6054* (2013.01); *A61M 2205/702* (2013.01); *A61M 2230/63* (2013.01); *A61M 16/0006* (2013.01)
USPC ............. 128/203.12; 128/204.25; 128/205.24

(58) Field of Classification Search
USPC .......................... 128/204.23, 200.14–200.22, 128/203.12–203.14, 204.18, 204.21, 128/204.24, 204.25, 205.18, 205.24
See application file for complete search history.

(56) References Cited

U.S. PATENT DOCUMENTS 3,234,932 A * 2/1966 Bird et al. ................ 128/204.25
3,523,527 A    8/1970 Foster
(Continued)

FOREIGN PATENT DOCUMENTS

CN    2172128 Y    7/1994
JP    11-267221 A  10/1999
(Continued)

OTHER PUBLICATIONS

PCT Search Report mailed Jan. 9, 2009, 9 pgs.
(Continued)

*Primary Examiner* — Tan-Uyen (Jackie) T Ho
*Assistant Examiner* — Mark K Han
(74) *Attorney, Agent, or Firm* — McDermott Will & Emery LLP

(57) ABSTRACT

A patient interface assembly includes a housing that defines an inlet port and an outlet port. A jet pump receives pressurized gas flow from the inlet port and delivers the gas flow to the outlet port. A nebulizer is fluidly coupled to the outlet port and positioned to introduce medication into the gas flow and deliver medicated gas flow to a patient.

20 Claims, 21 Drawing Sheets

(51) Int. Cl.
*A61M 16/00* (2006.01)
*A61M 16/08* (2006.01)
*A61M 16/12* (2006.01)
*A61M 11/06* (2006.01)

(56) References Cited

U.S. PATENT DOCUMENTS

| | | | |
|---|---|---|---|
| 3,580,249 A | 5/1971 | Takaoka | |
| 3,630,196 A * | 12/1971 | Bird et al. | 128/200.18 |
| 3,789,843 A | 2/1974 | Armstrong et al. | |
| 3,802,417 A | 4/1974 | Lang | |
| 4,224,940 A | 9/1980 | Monnier | |
| 4,228,795 A | 10/1980 | Babington | |
| 4,409,977 A | 10/1983 | Bisera et al. | |
| 4,424,806 A | 1/1984 | Newman et al. | |
| 4,436,090 A | 3/1984 | Darling | |
| 4,481,944 A | 11/1984 | Bunnell | |
| 4,520,812 A | 6/1985 | Freitag et al. | |
| 4,582,058 A | 4/1986 | Depel et al. | |
| 4,617,924 A | 10/1986 | Heim et al. | |
| 4,637,386 A | 1/1987 | Baum | |
| 4,693,242 A | 9/1987 | Biard | |
| 4,694,825 A | 9/1987 | Slemmer et al. | |
| 4,747,402 A | 5/1988 | Reese et al. | |
| 4,805,612 A | 2/1989 | Jensen | |
| 4,821,709 A | 4/1989 | Jensen | |
| 4,838,257 A | 6/1989 | Hatch | |
| 4,838,259 A | 6/1989 | Gluck et al. | |
| 4,889,115 A | 12/1989 | Bozano | |
| 5,002,050 A | 3/1991 | McGinnis | |
| 5,031,610 A | 7/1991 | Armstrong et al. | |
| 5,042,473 A | 8/1991 | Lewis | |
| 5,099,833 A | 3/1992 | Michaels | |
| 5,103,814 A | 4/1992 | Maher | |
| 5,116,088 A * | 5/1992 | Bird | 285/319 |
| 5,161,524 A | 11/1992 | Evans | |
| 5,165,398 A | 11/1992 | Bird | |
| 5,183,038 A | 2/1993 | Hoffman et al. | |
| 5,186,166 A | 2/1993 | Riggs et al. | |
| 5,188,098 A | 2/1993 | Hoffman et al. | |
| 5,217,004 A | 6/1993 | Blasnik et al. | |
| 5,239,994 A | 8/1993 | Atkins | |
| 5,265,594 A | 11/1993 | Olsson et al. | |
| 5,303,698 A | 4/1994 | Tobia et al. | |
| 5,307,794 A | 5/1994 | Rauterkus et al. | |
| 5,355,872 A | 10/1994 | Riggs et al. | |
| 5,377,671 A | 1/1995 | Biondi et al. | |
| 5,381,829 A | 1/1995 | Adahan | |
| 5,388,571 A | 2/1995 | Roberts et al. | |
| 5,423,313 A | 6/1995 | Olsson et al. | |
| 5,464,009 A | 11/1995 | Tatarek-Gintowt | |
| 5,479,920 A | 1/1996 | Piper et al. | |
| 5,482,058 A | 1/1996 | Garconnet | |
| 5,555,880 A | 9/1996 | Winter et al. | |
| 5,569,170 A | 10/1996 | Hansen | |
| 5,606,968 A | 3/1997 | Mang | |
| 5,692,497 A | 12/1997 | Schnitzer et al. | |
| 5,735,269 A | 4/1998 | Preece | |
| 5,752,506 A | 5/1998 | Richardson | |
| 5,752,507 A | 5/1998 | Moalem | |
| 5,769,797 A | 6/1998 | Van Brunt et al. | |
| 5,803,078 A | 9/1998 | Brauner | |
| 5,862,802 A | 1/1999 | Bird | |
| 5,896,853 A | 4/1999 | Howlett | |
| 5,901,705 A | 5/1999 | Leagre | |
| 5,927,274 A | 7/1999 | Servidio et al. | |
| 5,988,166 A | 11/1999 | Hayek | |
| 6,029,660 A | 2/2000 | Calluaud et al. | |
| 6,058,932 A | 5/2000 | Hughes | |
| 6,082,355 A | 7/2000 | Howlett | |
| 6,131,571 A | 10/2000 | Lampotang et al. | |
| 6,167,881 B1 | 1/2001 | Hughes | |
| 6,193,751 B1 | 2/2001 | Singer | |
| 6,203,502 B1 | 3/2001 | Hilgendorf et al. | |
| 6,279,574 B1 | 8/2001 | Richardson et al. | |
| 6,340,025 B1 | 1/2002 | Van Brunt | |
| 6,401,714 B1 | 6/2002 | Giorgini | |
| 6,415,791 B1 | 7/2002 | Van Brunt | |
| 6,435,182 B1 | 8/2002 | Lutchen et al. | |
| 6,505,622 B2 | 1/2003 | Py | |
| 6,547,749 B2 | 4/2003 | Hansen | |
| 6,571,798 B1 | 6/2003 | Thornton | |
| 6,581,600 B2 | 6/2003 | Bird | |
| 6,584,977 B1 | 7/2003 | Serowski | |
| 6,595,203 B1 | 7/2003 | Bird | |
| 6,681,767 B1 | 1/2004 | Patton et al. | |
| 6,694,977 B1 | 2/2004 | Federowicz et al. | |
| 6,694,978 B1 | 2/2004 | Bennarsten | |
| 6,701,926 B2 | 3/2004 | Olsen et al. | |
| 6,726,598 B1 | 4/2004 | Jarvis et al. | |
| 6,729,328 B2 | 5/2004 | Goldemann | |
| 6,805,118 B2 | 10/2004 | Brooker et al. | |
| 6,910,479 B1 | 6/2005 | Van Brunt | |
| 6,958,046 B2 | 10/2005 | Warwick et al. | |
| 6,968,843 B2 | 11/2005 | Krueger et al. | |
| 7,051,731 B1 | 5/2006 | Rogerson | |
| 7,066,177 B2 | 6/2006 | Pittaway et al. | |
| 7,115,104 B2 | 10/2006 | Van Brunt et al. | |
| 7,121,808 B2 | 10/2006 | Van Brunt et al. | |
| 7,128,069 B2 | 10/2006 | Farrugia et al. | |
| 7,131,439 B2 | 11/2006 | Blacker et al. | |
| 7,152,598 B2 | 12/2006 | Morris et al. | |
| 7,188,621 B2 | 3/2007 | Devries et al. | |
| 7,191,780 B2 | 3/2007 | Faram | |
| 7,267,121 B2 | 9/2007 | Ivri | |
| 7,270,128 B2 | 9/2007 | Berthon-Jones et al. | |
| 7,322,349 B2 | 1/2008 | Power | |
| 7,331,339 B2 | 2/2008 | Smith et al. | |
| 2001/0020473 A1 | 9/2001 | Bennarsten | |
| 2004/0025869 A1 | 2/2004 | Stradella | |
| 2005/0005936 A1 | 1/2005 | Wondka | |
| 2005/0103340 A1 | 5/2005 | Wondka | |
| 2005/0199237 A1 | 9/2005 | Lurie | |
| 2005/0229927 A1 | 10/2005 | Fink et al. | |
| 2005/0235988 A1 | 10/2005 | Hansen et al. | |
| 2006/0011198 A1 | 1/2006 | Matarasso | |
| 2006/0249155 A1 | 11/2006 | Gambone | |
| 2007/0056587 A1 * | 3/2007 | Travan | 128/204.18 |
| 2007/0074724 A1 | 4/2007 | Duquette et al. | |
| 2007/0093731 A1 | 4/2007 | Warwick et al. | |
| 2007/0101999 A1 | 5/2007 | Duquette et al. | |
| 2007/0125387 A1 | 6/2007 | Zollinger et al. | |
| 2007/0144519 A1 | 6/2007 | Henry et al. | |
| 2007/0144525 A1 | 6/2007 | Davidson et al. | |
| 2007/0215146 A1 | 9/2007 | Douglas et al. | |
| 2007/0227535 A1 | 10/2007 | Harrington et al. | |
| 2007/0246045 A1 | 10/2007 | Hoffman | |
| 2007/0277825 A1 * | 12/2007 | Bordewick et al. | 128/204.23 |

FOREIGN PATENT DOCUMENTS

| | | |
|---|---|---|
| RU | 2146153 C1 | 3/2000 |
| WO | 2006105980 A1 | 10/2006 |

OTHER PUBLICATIONS

PCT Search Report, 10 pgs.
Office Action for JP 2010-535046 dated Feb. 19, 2013.
Extended European Search Report for European Application No. 08851617.4.

* cited by examiner

PATIENT INTERFACE ASSEMBLY FOR RESPIRATORY THERAPY

CROSS REFERENCE TO RELATED APPLICATIONS

This Application is based on and claims the benefit of U.S. Provisional Patent Application Ser. No. 60/988,977, filed on Nov. 19, 2007, entitled "Respiratory Therapy System With Electromechanical Driver", and is related to U.S. patent application Ser. No. 12/274,066, filed on Nov. 19, 2008, entitled "Respiratory Therapy System With Electromechanical Driver", filed on even date herewith, the contents of which are both hereby incorporated by reference in their entirety.

BACKGROUND

The present disclosure relates to respiratory therapy systems and devices. More particularly, it relates to patient interface assemblies configured to couple to respiratory therapy systems for delivery of medication.

A wide variety of respiratory therapy devices are currently available for assisting, treating, or improving a patient's respiratory health. For example, positive airway pressure (PAP) has long been recognized to be an effective tool in promoting bronchial hygiene by facilitating improved oxygenation, increased lung volumes, and reduced venous return in patients with congestive heart failure. More recently, PAP has been recognized as useful in promoting mobilization and clearance of secretions (e.g., mucous) from a patient's lungs. In this regard, expiratory positive airway pressure (EPAP) in the form of high frequency oscillation (HFO) of the patient's air column is a recognized technique that facilitates secretion removal. In general terms, HFO reduces the viscosity of sputum in vitro, which in turn has a positive effect on clearance induced by an in vitro simulated cough. HFO can be delivered or created via a force applied to the patient's chest wall (i.e., chest physical therapy (CPT)), or by applying forces directly to the patient's airway (i.e., breathing treatment, such as high frequency airway oscillation). Many patients and caregivers prefer the breathing treatment approach as it is less obtrusive and more easily administered. To this end, PAP bronchial hygiene techniques have emerged as an effective alternative to CPT for expanding the lungs and mobilizing secretions.

Various HFO treatment systems are available for providing the respiratory therapy (high frequency intrapulmonary percussive therapy) described above (as well as other therapies and/or ventilation). In general terms, the high frequency intrapulmonary percussive (HFIP) system includes a hand-held device establishing a patient breathing circuit to which a source of positive pressure gas (e.g., air, oxygen, etc.) is fluidly connected. In this regard, the system further includes a driver unit that acts upon the supplied positive pressure gas, creating an oscillatory pressure profile or otherwise effectuate intermittent flow of gas into the patient breathing circuit, and thus percussive ventilation of the patient's lungs. With this approach, the patient breaths through the breathing circuit's mouthpiece (or mask), that in turn delivers the generated high-flow, "mini-bursts" of gas to the patient's airways. The pulsatile percussive airflow periodically increases the patient's airway pressure.

Current HFO treatment systems can also be used with a nebulizer to deliver aerosolized medication to patients. The nebulizer can be fluidly coupled to the driver unit to deliver medicated gas to patients through the patient interface circuit. Conventional configurations of patient interface circuits entrain medication within a device with ambient air to deliver the medicated gas to the patient. These configurations can contribute to medication "knock down", wherein build-up of medication within the device increases and the amount of medication delivered to the patient is reduced. Thus, a need exists for improved respiratory therapy systems, in particular patient interface assemblies that deliver medication to a patient.

SUMMARY

Concepts presented herein relate to a patient interface assembly for delivering respiratory therapy to a patient. The assembly includes a housing defining an inlet port and an outlet port. The inlet port is coupleable to a driver unit to receive pressurized gas flow produced by the driver unit. A jet pump disposed within the housing receives pressurized gas flow from the inlet port and delivers the pressurized gas flow to the outlet port. A nebulizer is fluidly coupled to the outlet port to receive pressurized gas flow, introduce medication into the gas flow and deliver medicated gas flow to the patient.

Aspects of the patient interface assembly can further be incorporated into a system and method to provide respiratory therapy. Additionally, other aspects can be added, removed and/or modified to the assembly. For example, the housing can include one or more of an entrainment port, exhalation port, nebulizer port and a pressure port. Further, the jet pump can be slidable within the housing and include an entrainment region, a throat region and/or an expansion region.

DETAILED DESCRIPTION

Figure 1:
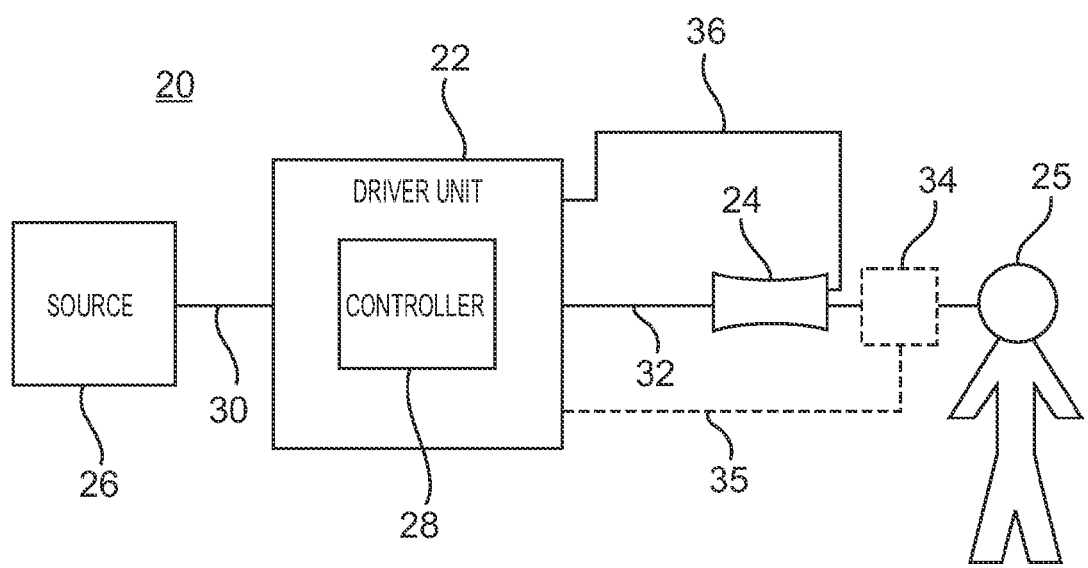
FIG. 1 is a schematic illustration of a respiratory therapy system.

FIG. 1 is a schematic illustration of one embodiment of a respiratory therapy system 20 including a driver unit 22 and a patient interface device 24 that serves as a patient interface circuit, establishing a breathing conduit to and from a patient 25 during use. In particular, the breathing conduit extends to an airway of the patient 25 (e.g. mouth, nasal sinuses). In one embodiment, the breathing conduit to the airway can be established with patient 25 through intubation. Additionally, if desired, the system 20 can be used with or without a ventilator. Details of the various components are described below. In general terms, however, the driver unit 22 is adapted for fluid connection to a source 26 (referenced generally) of pressurized gas (e.g., air, oxygen, etc.), and includes a controller 28 that controls operation of one or more electronic valves fluidly disposed between an inlet line 30 and an outlet line 32. More particularly, pressurized gas flow from the source 26 at the inlet line 30 is acted upon by the electronic valve(s) to create or supply a desired flow/pressure to the patient interface device 24 via the outlet line 32.

As described below, the driver unit 22 can include a number of different components or features, and the system 20 can include other, optional components, such as a nebulizer 34. One type of nebulizer that can be used in system 20 is an AirLife® Brand Misty Max 10™ nebulizer, available from Cardinal Health of Dublin, Ohio. In the case of use of nebulizer 34, an auxiliary line 35 extends from the driver unit 22 to the nebulizer 34. Controller 28 can be used to operate drive unit 22 to supply a desired flow/pressure to the nebulizer 34 via the auxiliary line 35. Regardless, the system 20 is capable of providing high frequency pressure pulses to the patient (e.g., percussive therapy) via operation of the driver unit 22, and offers a larger range of deliverable frequencies and pressures as compared to conventional, pneumatic valve-based driver units. A patient pressure line 36 can be provided to fluidly connect the patient interface device back to the driver unit 22 such that pressure within the patient interface device 24 can be measured and/or monitored. Controller 28 can be configured to control delivery of air to the patient 25 based on pressure measured in the patient interface device 24. Driver unit 22 can include further electronic valve(s) that operate to, for example, purge patient pressure line 36 and thus prevent excessive build up of fluids within the patient pressure line 36, allow auto zeroing of a pressure sensor, etc. In one embodiment, driver unit 22 can be connected to a central processing station, for example a nurse's station, to deliver information regarding operation of driver unit 22 and/or other information associated with the patient.

Figure 2:
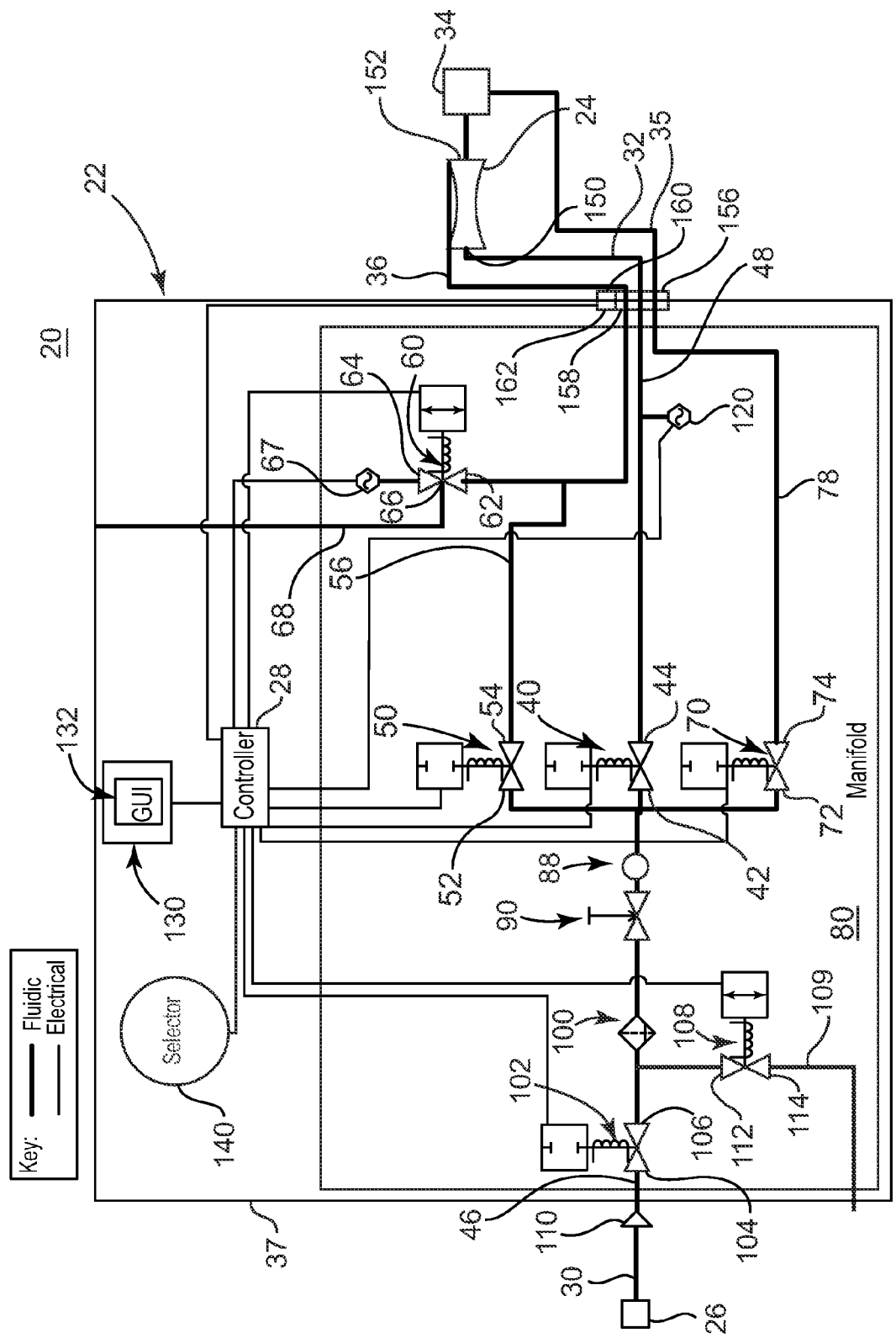
FIGS. 2-14 are schematic illustrations of other respiratory therapy systems.

As illustrated with more particularity in FIG. 2, the driver unit 22 can include a number of other components in addition to the controller 28, each of which are maintained in or by a portable housing 37. For example, with the one configuration of FIG. 2, the driver unit 22 includes an electronic valve 40 (e.g. a proportional solenoid valve) configured to act upon supplied pressurized gas in creating continuous high frequency pressure pulses. Alternatively, multiple on-off type solenoid valves can also be used to supplement and/or replace electronic valve 40. The electronic valve 40 can also be configured to selectively act upon supplied pressurized gas to effectuate delivery of a baseline pressure, positive airway pressure (PAP), continuous positive airway pressure (CPAP), etc. Other forms of positive airway pressure can also be used, such as bilevel PAP (BiPAP), which provides two levels of pressure. In any event, PAP is controlled from a manifold sensor in driver unit 22, while CPAP is controlled from a patient pressure sensor fluidly coupled to patient pressure line 36. The electronic valve 40 is fluidly connected between the inlet line 30 and the outlet line 32, and is electronically coupled to the controller 28. Thus, the controller 28 controls operation of the electronic valve 40 based upon programming maintained by the controller 28 (e.g., software and/or hardware). In this regard, the controller 28 can control delivery of power to the electronic valve 40 (as well as other components described below), with a power supply (not shown) being electrically coupled to the controller 28. The power supply can take a variety of forms, such as a battery maintained in the housing 37, a power cord for connection to a conventional wall power source, etc.

The electronic valve 40 includes or defines an inlet side 42 and an outlet side 44. Inlet side 42 is fluidly connected to an internal inlet line 46 that is internal to housing 37, whereas the outlet side 44 is fluidly connected to an internal outlet line 48 internal to housing 37. Internal inlet line 46 is fluidly coupled to inlet line 30 and internal outlet line 48 is fluidly coupled to outlet line 32. With this construction, then, gas flow provided to the inlet line 30 is delivered to the electronic valve 40. The electronic valve 40 can assume a variety of forms appropriate for introducing or creating high frequency pressure pulses when acting upon pressurized gas flow from the source 26. More particular, with embodiments in which the system 20 is adapted for use with "standard" source gas pressures provided at hospitals (e.g., oxygen or air maintained at a pressure in the range of 40-70 psi), the electronic valve 40 is configured to repeatedly open and obstruct an internal orifice (i.e., permit and prevent passage of gas therethrough) in response to signals from the controller 28 to create a pulse pressure flow over a large range of frequencies and pressures. For example, with some configurations, the electronic valve 40 is capable of generating pressure pulses at frequencies in the range of 1-25 Hz. Other frequencies can also be achieved, such as below 1 Hz and/or greater than 25 Hz (for example, as high as 30 Hz or 40 Hz).

As compared to conventional pneumatic shuttle valve-based driver units, the electronic valve 40 of the present disclosure provides a marked advantage in terms of more precise control and increased operational frequency and pressure ranges. Additionally, pneumatic valves require charging, thereby providing a large initial pressure pulse to the patient. Further, by electronically controlling the electronic valve 40, any change in gas pressure at the source 26 has little or no effect on the pulse profile generated by the electronic valve 40, thereby delivering consistent therapy while avoiding unexpected high pressures. Even further, the electronically-controlled valve 40 will not "stall" during an oscillatory pressure mode of operation, thus avoiding the problematic, unexpected delivery of high constant pressure to a patient found with available pneumatic valve driver units. In addition, by monitoring parameters within driver unit 22, driver unit 22 can increase safety by preventing undesirable situations and/or provide alarms to alert a caregiver. The electronic valve 40 can also be provided for effectuating a continuous, positive airway pressure when desired. Electronic valve 40 can further be configured to reduce dead volume. In one particular embodiment, dead volume is reduced to less than two cubic inches.

In addition to the electronic valve 40 described above, the driver unit 22 includes an optional purge electronic valve 50 that is electronically coupled to, and controlled by, the controller 28. In one embodiment, purge electronic valve 50 can be a solenoid valve. With the one construction of FIG. 2, the purge electronic valve 50 is fluidly connected to the interior inlet line 46 in parallel with the electronic valve 40 and serves to purge patient pressure line 36 leading from the patient interface 24 to the driver unit 22. The purge electronic valve 50 has an inlet side 52 fluidly connected to the interior inlet line 46, and an outlet side 54 fluidly connected to a purge line 56. The purge line 56 is fluidly coupled to patient pressure line 36 such that purge electronic valve 50 can be operated to clear patient pressure line 36 of fluids that may build up, in particular liquid and/or other particles exhausted from the patient 25.

To this end, a patient sensor autozero electronic valve 60 (e.g. a solenoid valve) can be provided to work cooperatively with the purge electronic valve 50. Autozero electronic valve 60 is electronically coupled to, and controlled by, the controller 28 and includes an inlet side 62, an outlet side 64 and an exhaust side 66. During normal operation, autozero electronic valve 60 is in a normally "open" position, allowing fluid to flow from patient pressure line 36 to a patient pressure sensor 67, which is discussed in more detail below. When patient pressure line 36 is purged, autozero electronic valve 60 is closed and patient pressure sensor 67 is fluidly coupled to a vent line 68, which is open to ambient (e.g., fluidly open to an exterior of housing 37). Next, purge valve 50 is opened, allowing patient pressure line 36 to be purged. Once patient pressure line 36 has been purged, and purge valve 50 is closed, autozero electronic valve 60 is opened as in normal operation.

Autozero electronic valve 60 can also be utilized to calibrate patient sensor 67, for example upon start up of system 20. To calibrate patient pressure sensor 67, autozero electronic valve 60 is closed such that pressure sensor 67 should read ambient pressure, as it is fluidly connected to ambient via vent line 68. Otherwise, patient pressure sensor 67 can be adjusted to a known reference ambient pressure. If desired, patient pressure line 36 can be purged during this adjustment. After calibration, autozero electronic valve 60 is opened as in normal operation.

An additional, optional feature of the driver unit 22 is an auxiliary valve 70. The auxiliary valve 70 can be electronic (e.g. solenoid) or pneumatic. The auxiliary valve 70 defines an inlet side 72 and an outlet side 74, and is electronically coupled to, and controlled by, the controller 28. The inlet side 72 is fluidly connected to the interior inlet line 46, in parallel with the electronic valve 40 and the purge electronic valve 50. However, the outlet side 74 is not connected to the interior outlet line 46. Instead, the outlet side 74 is fluidly connected to interior auxiliary line 78 that extends within the housing 37 for selective coupling to the auxiliary line 35. With this construction, then, the auxiliary valve 70 controls gas flow to the nebulizer 34, and thus can be referred to as the "neb flow valve". The nebulizer 34 is described in greater detail below. In general terms, however, in a nebulizer mode of operation, the controller 28 operates the neb flow valve 70 to an open state, thereby permitting gas flow to the nebulizer 34.

As shown in FIG. 2, the electronic valve 40, the purge electronic valve 50, the autozero electronic valve 60 and the neb flow valve 70 can be provided as part of, or connected to, a manifold 80. The manifold 80 effectively establishes three, parallel gas flow channels from the interior inlet line 46, with the electronic valve 40 permitting gas flow to the interior outlet line 48, the purge electronic valve 60 permitting gas flow to the feedback line 36 and with the neb flow valve 70 permitting gas flow to the auxiliary line 35 (via operation of the controller 28) as described above.

An optional volume chamber 88 can be provided along the interior inlet line 46 "upstream" of the valve 40. The volume chamber 88 acts as an accumulator or reservoir for storing fluid from inlet line 30. Thus, volume chamber 88 can reduce drop in pressure upon opening one or more of the valves 40, 50 and 70. For example, upon opening the purge electronic valve 50, fluid in volume chamber 88 can be utilized to reduce pressure drop from volume chamber 88 to inlet side 52 of purge electronic valve 50.

To account for possible pressure fluctuations from the gas source 26, the driver unit 22 can further include an optional pressure regulator 90 along the interior inlet line 46 "upstream" of the valve 40. The pressure regulator 90 can be a mechanical or electronically controlled device, configured to regulate incoming pressurized gas flow down to a desired pressure, thus maintaining a consistent therapeutic output from the system 20 regardless of the pressure provided at the source 26. As such, the driver unit 22 will generate consistent therapeutic outputs from hospital-to-hospital, it being recognized that the actual source 26 pressure will likely vary from location-to-location.

An additional optional feature provided with the driver unit 22 of FIG. 2 is a filter 100 fluidly connected to the interior inlet line 46 "upstream" of the valve 40. The filter 100 can assume a variety of forms, and is generally configured to remove debris or moisture entrained in the gas flow from the source 26. In some embodiments, the filter 100 is a water trap-type, and is fluidly located upstream of the pressure regulator 90.

If desired, driver unit 22 can further include an input electronic (e.g. solenoid) valve 102 that defines an inlet side 104 and an outlet side 106. Input electronic valve 102 is fluidly connected to interior inlet line 46 "upstream" of the filter 100. Additionally, input electronic valve 102 is electronically coupled to, and controlled by, controller 28. Input electronic valve 102 can be operated as an emergency "shutoff" valve and be operated to a closed state in instances where an internal pressure above a preset limit exists or a patient pressure exceeds a predefined value, closing flow to driver unit 22. The input electronic valve 102 is in the "normally closed" position and will selectively operate to permit fluid to pass from inlet side 104 to outlet side 106 upon direction from controller 28. When driver 22 is not in operation, input electronic valve 102 is closed. As a result, risk of potential build up of pressure within manifold 80 and/or housing 37 can be reduced.

In a further embodiment, an electronic vent valve 108 and a vent line 109 can be fluidly coupled between interior inlet line 46 and ambient to prevent pressure build up in interior inlet line 46 by opening vent valve 108. Vent valve 108 can be an electronic valve that is electronically coupled to, and controlled by, controller 28. Vent valve 108 defines an inlet side 112 and an outlet side 114. Inlet side 112 is fluidly coupled to interior inlet line 46 and outlet side 114 is fluidly coupled to vent valve 109. The vent valve 108 is in the "normally open" position, allowing flow from inlet side 112 to outlet side 114. During normal operation of driver unit 22, vent valve 108 will be operated to the closed position by controller 28. In yet another embodiment, electronic valve 40, purge electronic valve 50 and/or neb flow valve 70 can be operated to reduce pressure in interior inlet line 46.

With some constructions, the driver unit 22 is adapted for acting upon gas from one or more different sources 26. For example, the source can be oxygen, pressurized air from a compressor, fractional oxygen from a blender, etc. Additionally, these sources may have several different types of connectors based on source type, standards for a particular country, etc. With this in mind, the inlet line 30 is optionally fluidly connected to one or more inlet connectors 110, with each of the connectors 110 configured for fluid connection to a separate supply source 26. For example, one of the connectors can establish a fluid connection to a source of pressurized oxygen, whereas another of the connectors can establish a fluid connection with a source of pressurized air, thereby allowing for blending of gas within the driver unit 22. In addition, connectors can be adapted to be coupled to a blender that delivers fractional inspired oxygen. In the embodiment illustrated, only a single one of the connectors 110 is provided and connected to inlet line 30. Connector 110 is then fluidly coupled to interior inlet line 46.

As referenced above, the controller 28 controls operations of the valves 40, 50, 60, 70, 102 and 108. In this regard, in some embodiments, the controller 28 utilizes feedback information in controlling operations. With this in mind, the driver unit 22 further includes an optional manifold pressure sensor 120 fluidly connected to the interior outlet line 48. The manifold pressure sensor 120 can assume a variety of forms capable of sensing gas pressure within the interior outlet line 48. Regardless, the manifold pressure sensor 120 is electronically coupled to the controller 28, signaling information indicative of the pressure sensed in the outlet line 32, and thus provides closed-loop feedback to the controller 28. In one example, manifold pressure sensor 120 is used to monitor whether a desired PAP level is being provided to the patient.

As mentioned above, patient pressure sensor 67 can also form and serve as an information source to controller 28. The patient pressure sensor 67 can assume a variety of forms, and is fluidly connected to the patient interface device 24 for sensing pressure within the patient interface device 24 through patient pressure line 36 and autozero electronic valve 60. As described in greater detail below, the patient interface device 24 can be configured to provide a convenient port for receiving patient pressure line 36 that in turn is fluidly coupled to the patient pressure sensor 67 (as retained by the housing 37). Regardless, the patient pressure sensor 67 is electronically coupled to the controller 28, and signals information indicative of a sensed pressure at the patient interface device 24. In one example, patient pressure sensor 67 is used to monitor whether a desired CPAP setting is being provided to the patient. Other parameters, such as flow or pulse volume delivered to the patient, can also be used to provide feedback to controller 28, if flow measuring or spirometry means are integrated into driver unit 22.

The driver unit 22 further optionally includes one or more display systems 130 for displaying information to a caregiver. In one example, display system 130 can be a liquid crystal display. The display system(s) are electronically coupled to, and controlled by, the controller 28, and can include a graphical user interface (GUI) 132. As described below, the GUI 132 can be operated to display various performance information (e.g., graphical depiction of a current pulse profile, minimum and maximum pressures, etc.).

The driver unit 22 includes a user input device (or interface) 140 that is electronically coupled to the controller 28. The user interface 140 serves as a selection indicator, affording the caregiver the ability to select a desired mode of operation as described below. Thus, the user interface 140 can assume a wide variety of forms, including mechanical (e.g., control knob) and/or visual (e.g., touchpad device) devices.

During use of the system 20, the inlet line 30 is fluidly connected to the supply source(s) 26 via the appropriate connector(s) 110. The patient interface device 24 is provided to the caregiver separate from the driver unit 22. Various possible configurations of the patient interface device 24 are described below. In general terms, however, the patient interface device 24 can be a disposable, hand-held product, including an inlet end 150 configured for fluid coupling to the outlet line 32 otherwise extending from the housing 37, and an outlet end 152 through which the patient breathes (with the outlet end 152 being connectable to (or forming) a patient breathing component such as a mouthpiece or mask). In one embodiment, outlet line 32, auxiliary line 35 and patient pressure line 36 are each formed of tubing that can be provided with the patient interface device 24.

Each of the lines 32, 35 and 36 can terminate at a connector piece 156 (referenced generally) sized for engagement within a corresponding connector port 158 of the driver unit 22. For example, the connector port 158 can be carried by the housing 37, and can establish fluid connections to the outlet line 32, the patient pressure line 36, and/or the auxiliary line 35 such that only a single connective step is required of the operator (i.e., insertion of the connector piece 156 into connector port 158). Alternatively, connector port 158 can be formed integral with the housing and/or manifold. In any event, the connector piece 156 can hold each of the lines 32, 25 and 36 in fixed relation for simple fluid connection to the driver unit 22. Furthermore, connector piece 156 can include a quick-release mechanism for easily securing and releasing connector piece 156 to and from connector port 158.

Connector piece 156 can further include an identifier stored on any type of storage medium 160, such as an RFID tag, that indicates capability with the driver unit 22. To this end, the driver unit 22 can further include a device 162 to receive information from storage medium 160, such as an RFID tag reader, electrically coupled to the controller 28. Storage medium 160 can include further information that can be transmitted to controller 28 through device 162. For example, storage medium 160 can be associated with a particular predetermined therapy protocol and thus controller 28 can be operated in conjunction with the desired therapy protocol. Additionally, other information can be stored on storage medium 160, such as patient information, compatibility information, etc. Alternatively, any other type of communication means can be utilized to deliver information associated with the patient interface device 24 to the driver unit 22. One example communication means that can be used is a contact serial interface such as 1-Wire® Serial Memory Products, provided by Maxim Integrated Products, Inc. of Sunnyvale, Calif. In this case, potential interference of radio frequency signals can be eliminated due to direct contact between host and slave hardware that creates the interface.

Regardless, with the patient interface device 24 fluidly connected to the outlet line 32 and, where provided, the patient pressure sensor 67 (via the patient pressure line 36), the caregiver then operates the driver unit 22 to deliver a respiratory therapy to the patient. In this regard, the driver unit 22 optionally offers at least six modes of operation, including an autozero mode, a percussive mode, a baseline mode, a positive airway pressure (PAP) mode, a purge mode and a nebulizer mode. Each of these modes can be implemented independent of the other, or two or more of the modes can be effectuated simultaneously. Each mode of operation is described in greater detail below. One or more of the modes can also be implemented by controller 28 as defined in a pre-defined protocol that can easily be implemented by a caregiver.

As a starting point, the driver unit 22 is optionally configured such that the electronic valves 40, 50, 70 and 102 default to a normally "closed" state in which gas flow through the respective valve 40, 50, 70 and 102 does not occur. The electronic valves 60 and 108 default to a normally "open" state in which gas flows through the valves 60, 108. In particular, outlet side 64 of valve 60 is fluidly coupled to inlet side 62 and outlet side 114 of valve 108 is fluidly coupled to inlet side 112. When system 20 is powered "on", the autozero mode can begin so as to calibrate patient pressure sensor 67. In autozero mode, autozero electronic valve 60 is closed, allowing patient pressure 67 to read ambient pressure since patient pressure sensor 67 is coupled to ambient via vent line 68. Based on the reading of patient pressure sensor 67, adjustments can be made such that patient pressure sensor 67 registers a known ambient pressure. Once patient pressure sensor 67 is adjusted as desired, autozero electronic valve 60 is opened.

Upon receiving an indication from a caregiver (via the user input 140) that a percussive mode is desired, the controller 28 operates the electronic valve 40 to rapidly open and close, thus imparting pressure pulses into the gas flow from the inlet line 30 to the outlet line 32. In this regard, the electromechanical configuration of the electronic valve 40 allows the controller 28 to achieve precise control over the delivered pressure pulse profile, which can be based off of readings from manifold pressure sensor 120. Thus, the pulsed gas flow delivered to the patient interface device 24, via the outlet line 32, can have one of many different frequencies and/or pressures commensurate with the operational capabilities of the electronic valve 40. If desired, the baseline mode can supplement the pulsed gas flow to maintain lung recruitment. As a point of reference, different frequencies and pressures have different effects on a patient. For example, frequencies around 20 Hz have been found to lower the viscosity of the mucous, whereas frequencies in the range of 8-15 Hz are commensurate with the normal cilia beat frequency range and thus work to mobilize secretions. Frequencies in the range of 2-5 Hz have been found to expand the lungs and deliver oxygen to the alveoli, as well as stimulate a "mini-cough" and shear mucous. Thus, depending upon a desired therapeutic result, the caregiver can (via the user interface 140) effectuate a desired protocol/frequency.

In some instances, the caregiver is aware of a desired protocol (e.g., in terms of pressure and/or frequency), and can enter the desired value(s) at the user interface 140 for subsequent implementation by the controller 28. With other embodiments, the controller 28 is pre-programmed with one or more potentially applicable protocol settings. For example, the controller 28 can include a memory in which a library of protocol settings is maintained. Selection of a protocol can be based on several factors. In one embodiment, if flow sensing and/or spirometry means are employed, protocol selection can be based on measurements obtained by these means. Upon selection of a desired protocol at the user interface 140, the controller 28 automatically "loads" the predetermined settings such that operation of the system 20 requires less training and easier set-up by the caregiver as compared to conventional driver units. For example, one predetermined desired protocol could comprise two minutes of PAP mode, followed by two minutes of 20 Hz percussive therapy, followed by two minutes of 2 Hz percussive therapy, etc.

Alternatively, or in addition to, storage medium 160 (e.g. an RFID tag) can store a particular desired setting that can be read by device 162 (e.g. an RFID reader) and communicated to controller 28. Further, the pre-programmed features ensure that consistent and uniform therapy will be provided to the patient independent of caregiver knowledge of the therapy. Due to the consistent and uniform therapy delivered, the caregiver can identify if changes in the patient airway has occurred given changes in patient pressure sensor 67 (e.g. increased lung recruitment). This is in direct contrast to current devices/drivers on the market that are not intuitive to set up or use. Some require needle valves that are manipulated by the caregiver to control the profile of the pulse. While attempting to change intensity in a pneumatic system, frequency will also change, making it difficult to independently alter intensity and frequency. Significant, unexpected changes in the resultant pulse profile may occur even when making only a small adjustment in the position of the needle valve. This makes it difficult for existing devices to deliver consistent, expected therapy.

In addition or as an alternative to the pre-programmed settings, the controller 28 can be programmed by the caregiver to store one or more desired therapy protocols. These programs can be entered by the caregiver or the caregiver's colleague (such as in a hospital setting) to ensure the exact same treatment procedures are followed throughout the hospital and amongst all of the respiratory therapists using the driver unit 22. If desired, this information can be directly stored on a storage medium and tailored as requested during manufacturing and/or assembly of driver unit 22. For example, different parameters can be utilized when preparing a system for pediatrics as opposed to adults, allowing for different therapy and/or alarm settings.

In addition to operating the electronic valve 40 based upon user-entered and/or predetermined settings, in some embodiments, the controller 28 is further programmed to perform an example routine in which a resonant frequency (where the most effective therapy is likely to occur) of the patient's lungs is "located." More particularly, the example routine includes the controller 28 operating the electronic valve 40 to initially generate higher frequency pulse rates (e.g., 20 Hz) and gradually decrease to a lower rate (e.g., 2 Hz). The process is then repeated at incrementally higher pressures. The rate can also decrease, if desired, by starting at a high frequency pulse rate and decreasing to a lower rate.

Throughout the example routine, the patient is monitored for chest wiggle, as is information signaled from the pressure sensors 67, 120, to determine the pulse rate frequency that best fits the resonant frequency, or "sweet spot," for a particular patient. In one embodiment, an accelerometer can be coupled to the patient's chest and provide a signal indicative of chest movement. This chest movement signal can be monitored based on the rate of frequency pulses delivered to identify an optimal frequency.

The percussive mode of operation can be supplemented by the baseline mode of operation. The baseline mode provides a desired pressure, wherein electronic valve 40 partially obstructs flow from interior inlet line 46 to interior outlet line 48. The pressure is provided to keep patient airways open during delivery of percussive therapy (e.g. between bursts of air flow).

As with the procedures described above, the controller 28 can be pre-programmed or preset with one or more therapy protocols that include operation of the electronic valve 40 in delivering PAP pressure to the patient. One example, non-limiting protocol program can include: 1) running the PAP mode low pressure for five minutes (i.e., the electronic valve 40 open); 2) operate the electronic valve 40 at 20 Hz, with low pressure for three minutes; 3) operate the electronic valve 40 to generate percussive pulses at a frequency of 2 Hz with low pressure for three minutes; and 4) operate the electronic valve 40 at a frequency of 5 Hz with high pressure for five minutes. A wide variety of other protocols are equally available.

Where a PAP therapy is desired, the controller 28, upon receiving a corresponding caregiver selection of the PAP mode at the user interface 140, operates the electronic valve 40 to "open" a desired extent. In this regard, the pressure desired for the PAP therapy can be selected (or pre-programmed) by the user, with the controller 28 monitoring information from the manifold pressure sensor 120 to determine whether the effectuated electronic valve 40 setting is achieving the desired pressure. Alternatively, or in addition to, CPAP, Bi-PAP, etc. therapy can be delivered based on information received from patient pressure sensor 67.

The purge mode can be performed in conjunction with the autozero mode described above. Additionally, the purge mode can be performed independent of the autozero mode. To purge patient pressure line 36, autozero electronic valve 60 is moved to a closed position, such that flow is shut off from inlet side 62 to outlet side 64. At this point, patient pressure sensor 67 is fluidly coupled to vent line 68, which exits the portable housing 37. Thus, patient pressure sensor 67 reads atmospheric pressure and its feedback to controller 28 can be delayed and/or patient pressure sensor 67 can be adjusted as discussed with respect to the autozero mode. The purge electronic valve 50 is then opened so that flow from inlet line 30 is used to purge patient pressure line 36 of liquid and/or other build up. After patient pressure line 36 has been purged, purge electronic valve 50 is closed and then autozero electronic valve 60 is moved to the open position, allowing flow to patient pressure sensor 67.

In the nebulizer mode, the nebulizer 34 is fluidly connected to the neb flow valve 70 (via the auxiliary line 35) as well as to the patient interface device 24. For example, the single connector 156 mentioned above can establish the necessary fluid connection to driver unit 22 through connector port 158. In some embodiments, the patient interface device 24 and the nebulizer 34 are constructed such that the nebulizer 34 fluidly connects to the outlet end 152 of the patient interface device 24, with the nebulizer 34 being provided apart from the driver unit 22. Regardless, by locating the nebulizer 34 "downstream" of the patient interface device 24, aerosolized medication generated by the nebulizer 34 does not pass through the patient interface device 24, thereby significantly reducing the possibility for aerosol knock-down within the geometry of the patient interface device 24. For example, configurations with the nebulizer 34 located "downstream" of the patient interface device 24 can deliver more than five times as much inhaled respirable mass (e.g. aerosolized medication) to a patient compared to conventional patient interface designs.

With the nebulizer 34 fluidly connected as described above, the controller 28, upon receiving a corresponding selection by the caregiver at the user interface 140, operates the neb flow valve 70 to permit gas flow to the auxiliary line 35, and thus to the nebulizer 34. In this regard, the controller 28 can maintain the electronic valve 40 in a closed state such that only nebulizer therapy is delivered to the patient. Alternatively, and as desired by the caregiver, the electronic valve 40 can simultaneously be operated (with the neb flow valve 70 at least partially open) to deliver aerosolized medication to the patient in conjunction with a percussive, percussive with baseline and/or PAP therapy, and/or during a predefined protocol.

During operation of the system 20 in delivering percussive, PAP or nebulizer therapy, the controller 28 is programmed to maintain desired output from the electronic valve 40 via information received from the patient pressure sensor 67 and/or the manifold pressure sensor 120. The manifold pressure sensor 120 provides feedback allowing the controller 28 to monitor the output of the electronic valve 40, thus creating a closed-loop system that enables the controller 28 to incrementally adjust operation of the valve 40 as necessary. This feature, in turn, assures that the desired or correct pulse pressure (or baseline pressure if in baseline mode) is consistently and constantly being delivered to the patient.

The patient pressure sensor 67 monitors the pressure being delivered to the patient. In instances where the controller 28 "determines" that the sensed patient pressure and/or manifold pressure exceeds a predetermined value, the controller 28 can automatically initiate operation of the electronic valves 40, 70 and/or 102 to a closed state. Additionally, pressure delivered to a patient can be adjusted based on pressure sensed by patient pressure sensor 67. In one example, patient inspiratory and expiratory phases of breathing can be detected using patient pressure sensor 67 and/or spirometry means that sends information to the controller 28. During a percussive mode of operation, percussive therapy can be delivered during the patient inspiratory phase by operating electronic valve 40 to deliver percussive pulses during the inspiratory phase. If a maximum patient pressure is known (e.g. as prescribed by a physician), electronic valve 40 can further be operated based on the maximum patient pressure and the inspiratory/expiratory phases. Alternatively, spirometry means can be used to detect patient breath and alter the delivery of therapy during either inspiratory or expiratory phased to maximize a desired effect.

Other measurement devices can also be employed to deliver information to controller 28 for display and/or to control operation of driver unit 22. For example, a spirometer can be utilized to measure a volume of air inspired and/or expired by the patient. The spirometer can be integrated into patient interface device 24 and utilized to determine patient progress (e.g., a higher volume of air expired by the patient may indicate patient improvement) due to the fact that a section of the lung has been cleared and/or recruited.

As indicated above, the display system 130 can be operated by the controller 28 to display various information to the caregiver as desired. In addition to displaying various operational control settings (e.g., operational mode, selected pressure(s) and/or frequency), the controller 28 can determine and display information indicative of or relating to the actual pressure or gas flow being delivered to the patient. For example, the controller 28 can be programmed to record pressures sensed by the patient pressure sensor 67 and calculate information, such as minimum, mean, maximum, and/or trending pressure, with this information being displayed on the display system 130. The display protocol can vary, and in some embodiments the controller 28 is programmed to update the displayed information periodically (e.g., once every second), with the maximum pressure recorded over the previous time period (e.g., second) of data acquisition.

The driver unit 22 can also include various optional alarm features operated by the controller 28. For example, if a pressure is detected at the manifold pressure sensor 120 and/or the patient pressure sensor 67 that exceeds a preset pressure limit, the controller 28 is programmed to operate the alarm (e.g., audible, visual) to alert the caregiver and to implement a step-down therapy protocol and optionally closing the electronic valves 40, 70 and 102. These alarms can be user adjustable to any type of setting for notification of events based on various situations (e.g., crossing an adjustable threshold).

The system 20 uniquely provides a plethora of features useful in delivering respiratory therapy to a patient. In other embodiments, features can be added, modified or eliminated as desired. For example, FIG. 3 provides a representation of a therapy system 170 where the purge electronic valve 50, the autozero electronic valve 60, the input electronic valve 102 and the vent electronic valve 108 have been eliminated, along with volume chamber 88. Additionally, the therapy system 170 includes multiple connectors 110 coupled to separate supply sources. One of the connectors can establish fluid connection with a source of pressurized oxygen whereas the other connector can establish a fluid connection with a source of pressurized air. Still further, one connector could be coupled to a source of fractional inspired oxygen as generated by a gas blender. In yet a further embodiment, a gas blender could be integrated into housing 37. In addition, the therapy system 170 includes a secondary electronic valve 172 and a vent valve 174.

Secondary electronic valve 172 can be configured similar to electronic valve 40 and is electronically coupled to, and controlled by, the controller 28. The electronic valve 40 and secondary electronic valve 172 can serve to operate to deliver percussive therapy and PAP therapy separately, such that one valve is used primarily for delivering percussive therapy and the other valve is used primarily for baseline and/or PAP therapy. Also, secondary electronic valve 172 can also be used to increase a range of intensity settings during percussive therapy as being operated in conjunction with the primary valve. Secondary electronic valve 172 can also be staggered with respect to electronic valve 40 to allow for higher frequency settings of percussive therapy delivery.

In the embodiment illustrated, the secondary electronic valve 172 is positioned in parallel with electronic valve 40 and neb flow valve 70. The secondary electronic valve includes an inlet side 176 fluidly coupled to interior inlet line 46 and an outlet side 178 fluidly coupled to interior outlet line 48. In FIG. 3, electronic valve 40 is configured to deliver percussive therapy while secondary electronic valve 172 is configured to deliver PAP therapy. Thus, controller 28 operates to drive electronic valve 40 when percussive therapy is desired and operates to drive secondary electronic valve 172 when PAP therapy is desired. Further, controller 28 can operate the secondary electronic valve 172 in an open (or partially open) state during percussive operation of the electronic valve 40 to provide percussive therapy in combination with a baseline pressure above ambient (e.g. the baseline mode).

The vent electronic valve 174 is electronically coupled to, and controlled by, the controller 28 and includes an inlet side 180 and an outlet side 182. The vent electronic valve 174 serves as an emergency "dump" valve with the inlet side 180 fluidly coupled to the interior outlet line 48 and the outlet side 182 fluidly connected to a vent line 184. The vent line 184 is open to ambient. In instances where the controller 28 determines that an internal pressure above a preset limit exists, the vent electronic valve 174 is operated to an open state, allowing gas flow in the interior outlet line 48 to exhaust from the system 170 (and thus not be delivered to the patient interface device 24 or the patient). Alternatively, the vent electronic valve 174 can be located in any position along either interior inlet line 46 or outlet interior line 48 and operated in either a "normally open" or "normally closed" state. For example, the vent electronic valve 174 can be located "upstream" of the proportional solenoid valves 40, 172 (e.g., along the interior inlet line 46 in a similar position as vent valve 108 in FIG. 2). Even further, the vent electronic valve 174 can be in-line with either of the interior inlet line 46 or the interior outlet line 48 (i.e., the inlet side 180 and the outlet side 182 are fluidly connected to the corresponding interior inlet line 46 or interior outlet line 48), operating in a normally "open" state. With this construction, upon determining existence of an excessive pressure condition, the controller 28 operates the electronic valve 174 to a closed state, thus preventing gas flow/pressure from being delivered to the patient.

Figure 4:
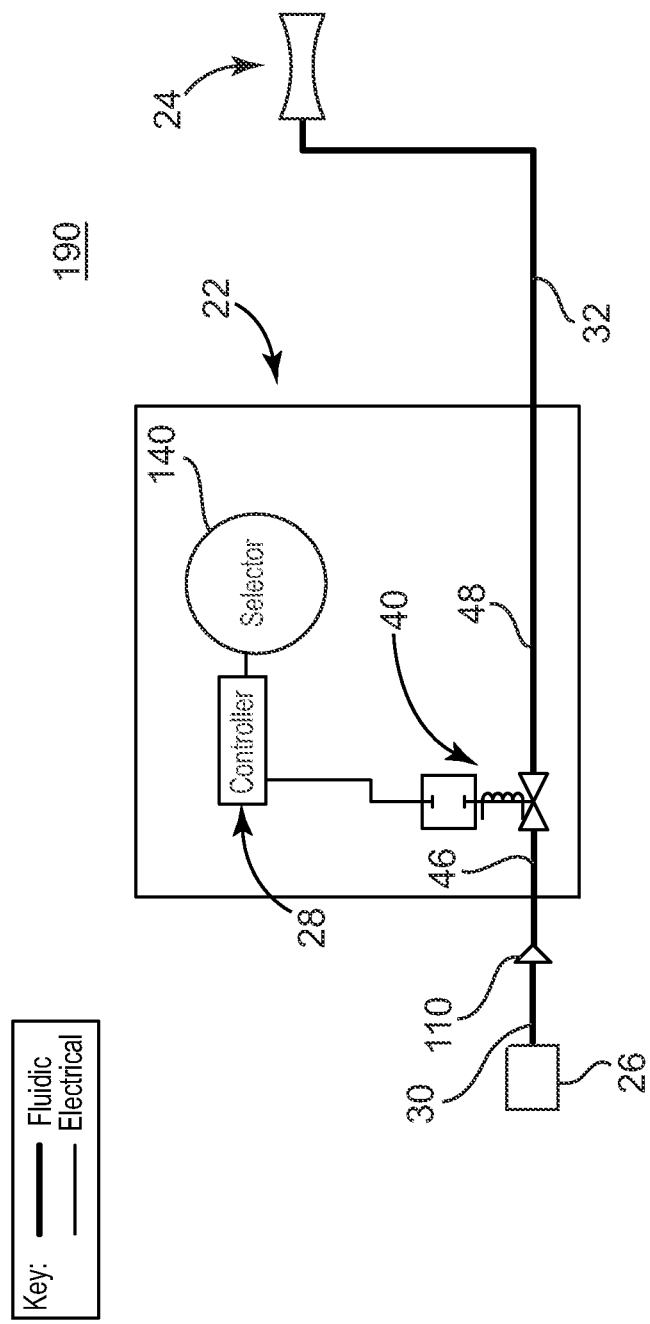

FIG. 4 provides a representation of a basic respiratory therapy system 190 in accordance with the present disclosure, and including some of the components of the system 20 (FIG. 2) described above. In particular, the system 190 includes the driver unit 22 and the patient interface 24. The driver unit 22, in turn, includes the controller 28 and the electronic valve 40. The electronic valve 40 regulates gas flow/pressure between the inlet line 30 and the outlet line 32. The controller 28 operates the electronic valve 40 to provide percussive therapy as described above. In addition, the controller 28 can optionally be further programmed to operate the electronic valve 40 to provide baseline pressure and/or positive airway pressure (PAP) if desired.

Figure 5:
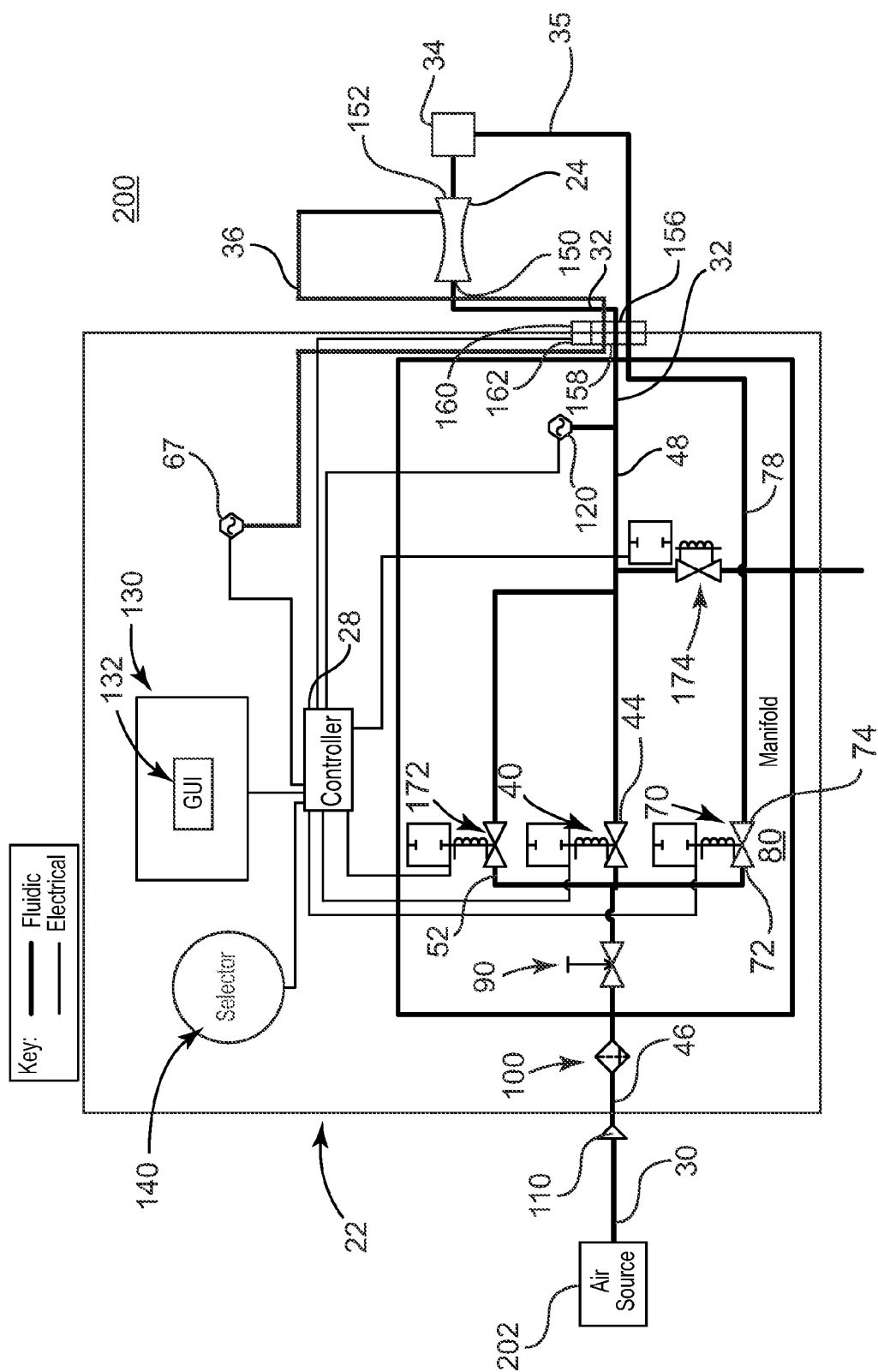

FIG. 5 schematically illustrates an alternative respiratory therapy system 200 in accordance with the present disclosure. The system 200 is akin to the system 170 (FIG. 3) described above, except that the driver unit 22 is configured for connection to only an air source 202. Thus, only a single connector 110 is provided (as compared to the two or more connectors 110 of FIG. 3).

Figure 6:
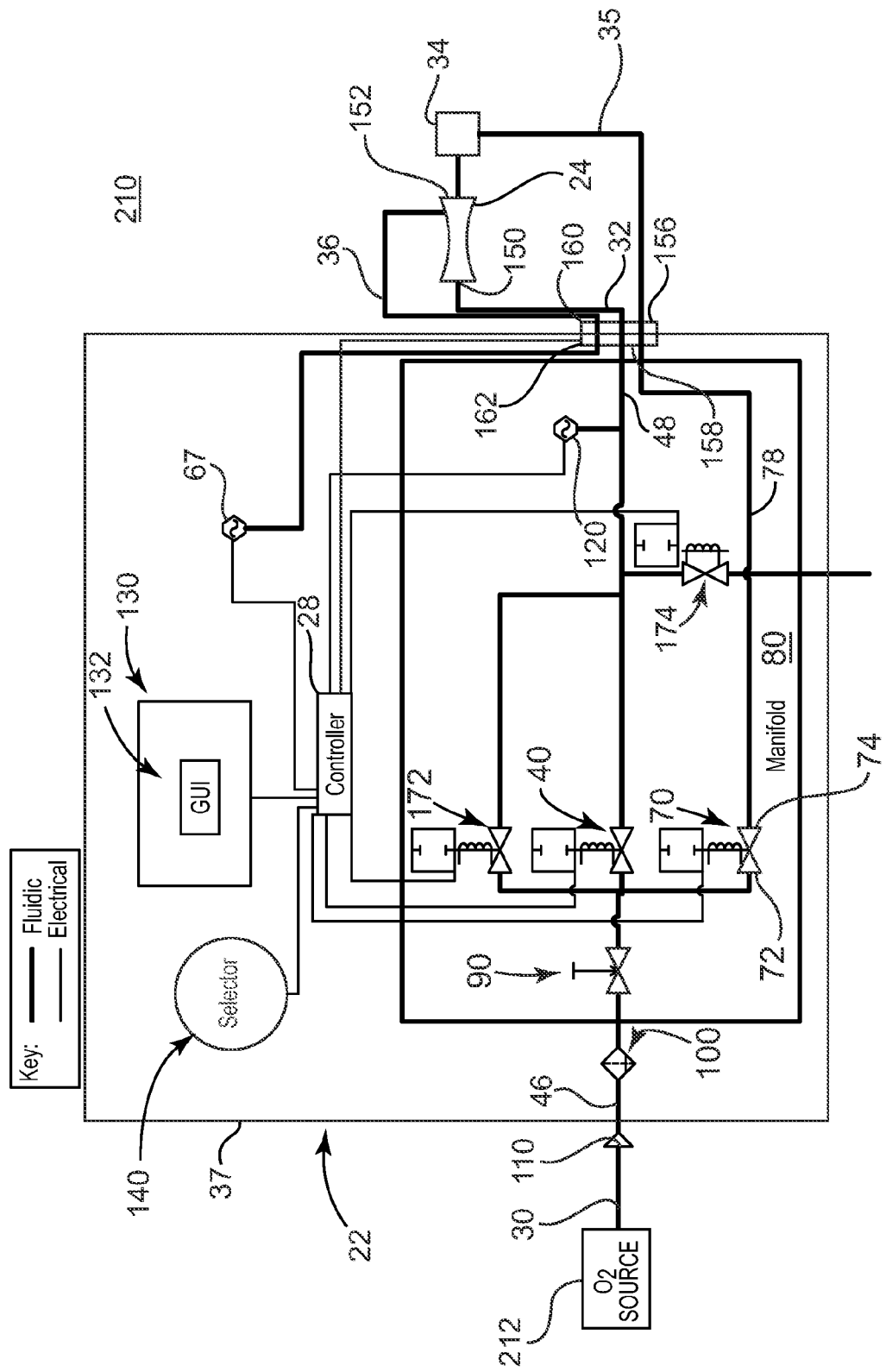

FIG. 6 illustrates another respiratory therapy system 210 analogous to the system 200, with the driver unit 22 configured for fluid connection only to an oxygen source 212.

Figure 7:
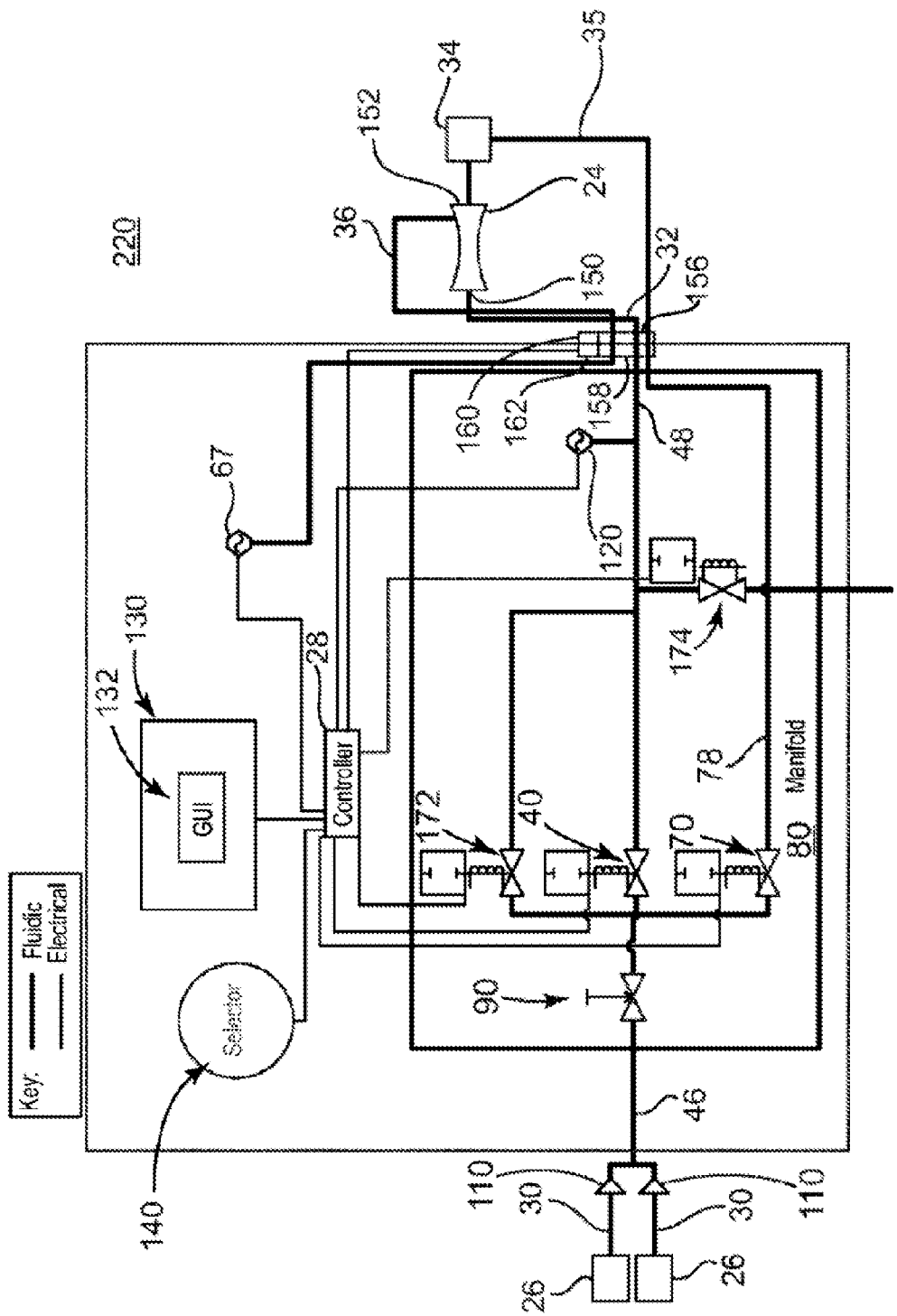

With the alternative construction of FIG. 7, a respiratory therapy system 220 is provided that is akin to the system 170 (FIG. 3) previously described, except that the filter 100 (FIG. 3) is eliminated.

Figure 3:
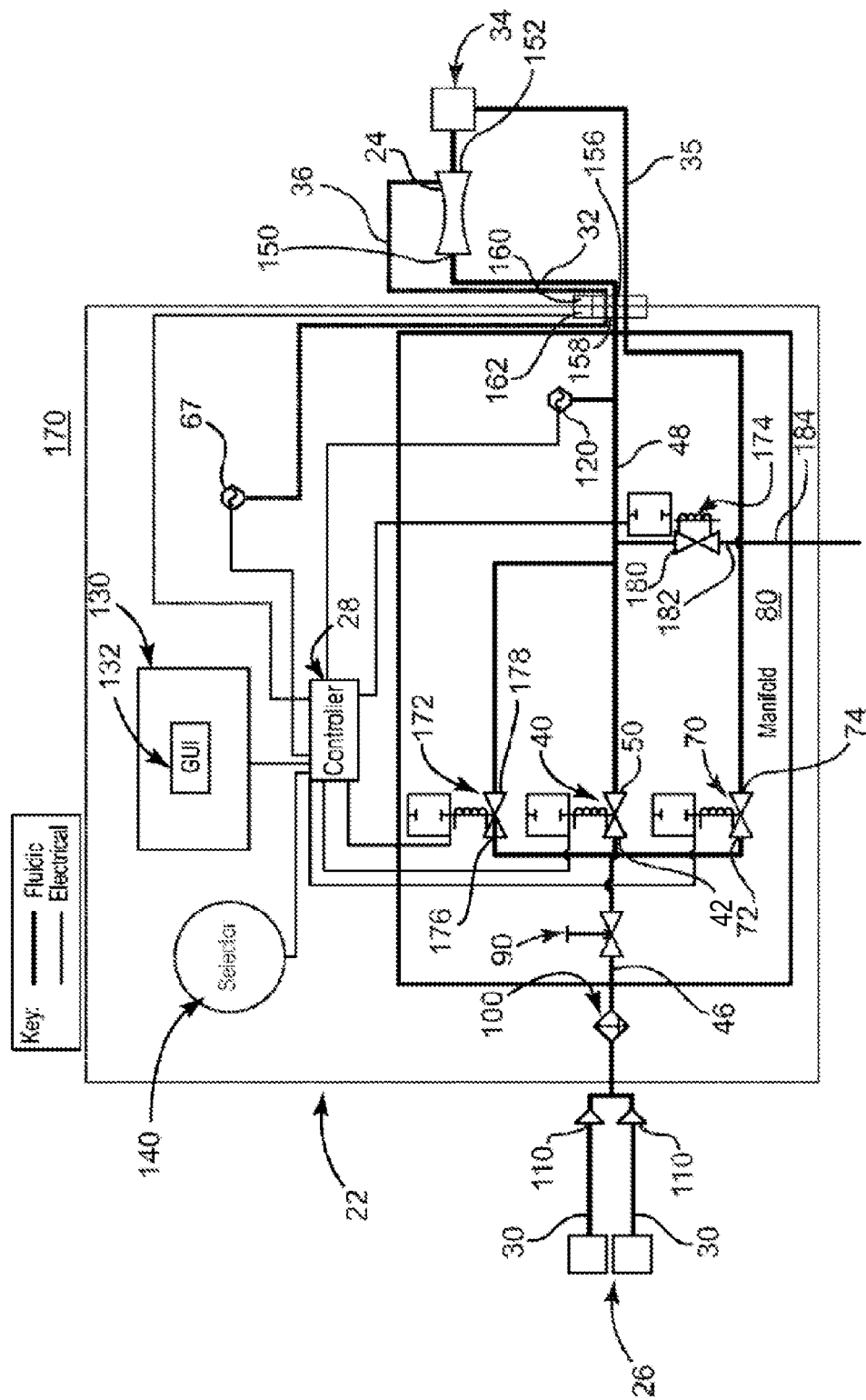
Figure 8:
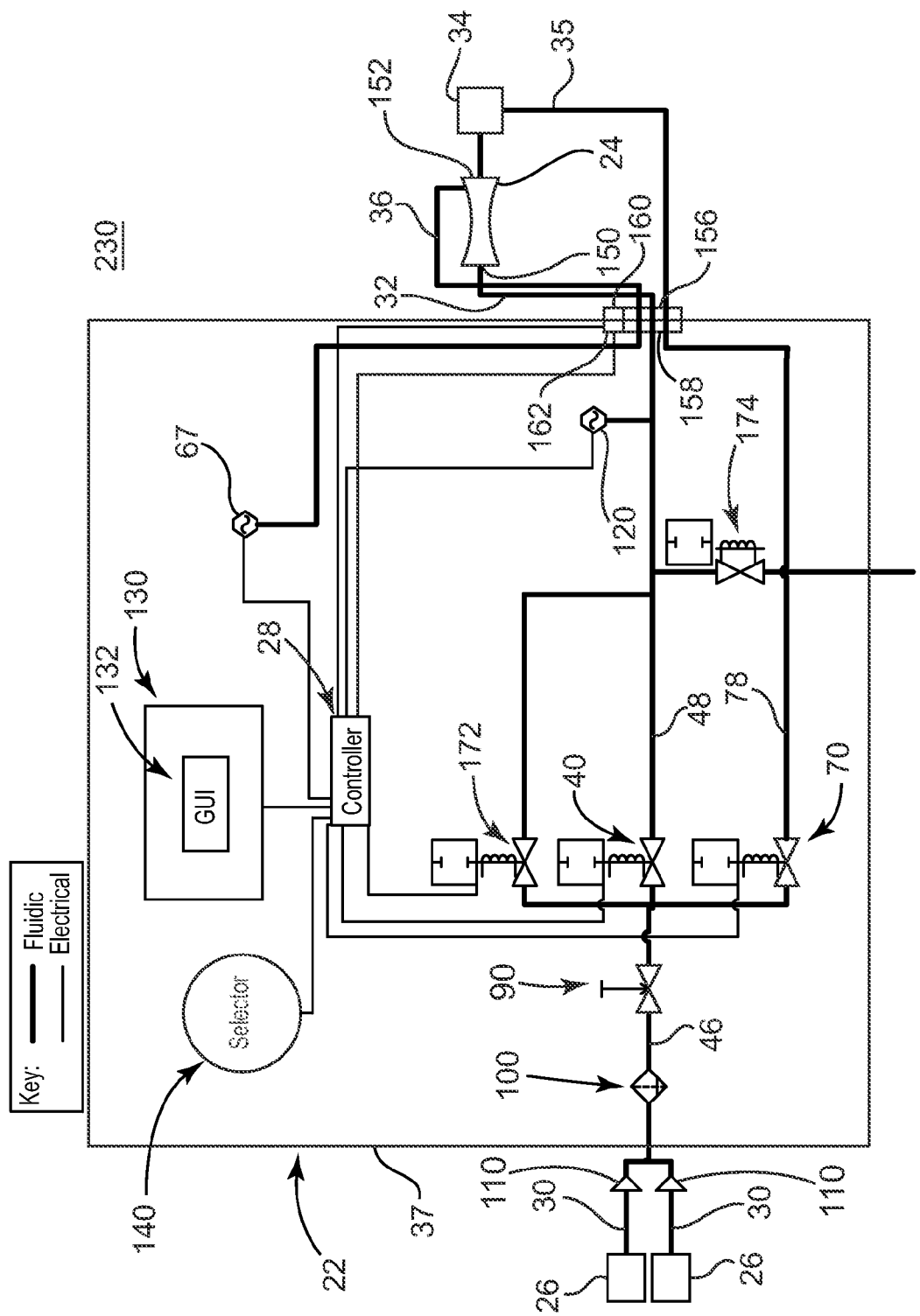

FIG. 8 illustrates another respiratory therapy system 230 akin to the system 170 of FIG. 3, except that the manifold 80 (FIG. 3) is eliminated. Thus, independent lines are employed to fluidly connect the electronic valve 40, the secondary electronic valve 172, and the neb flow valve 70 with the inlet line 30. Alternatively, a partial manifold can be provided, establishing fluid connections to only some of the valves (e.g., a manifold establishing fluid connection to only the electronic valves 40, 172 and the neb flow electronic valve 70).

Figure 9:
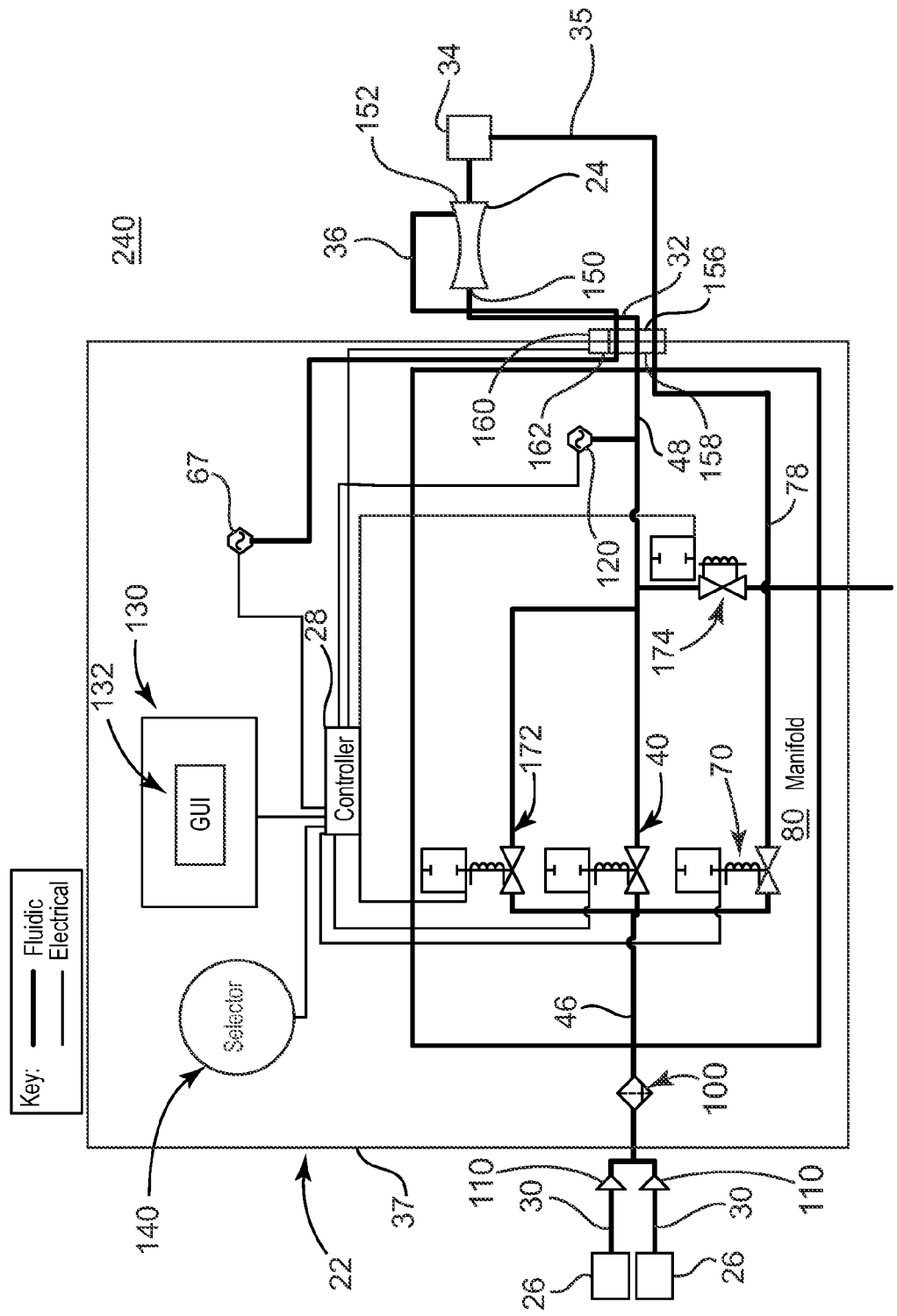

With the alternative respiratory therapy system 240 of FIG. 9, the optional pressure regulator 90 (FIG. 3) is eliminated. With this construction, incoming pressure control can optionally be accomplished by the controller 28 operating the electronic valve(s) 40 and/or 172 based on information generated at the patient pressure sensor 67 and/or manifold pressure sensor 120.

Figure 10:
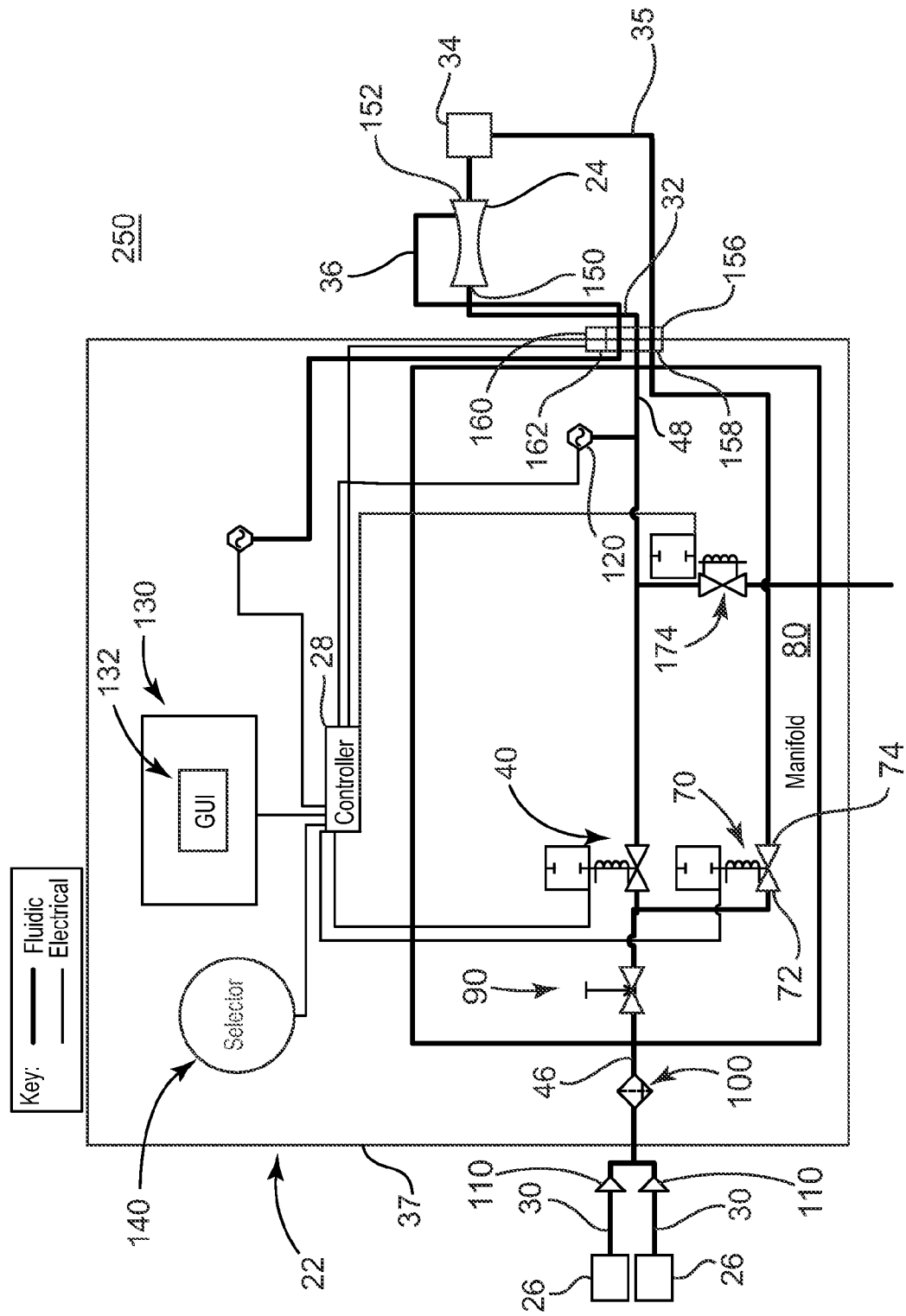

Yet another respiratory therapy system 250 is schematically illustrated in FIG. 10, and again is akin in many respects to the system 170 of FIG. 3. Unlike the system 170, however, the driver unit 22 omits the secondary electronic valve 172 (FIG. 3). With this construction, the electronic valve 40 can be operated by the controller 28 to provide positive airways pressure (PAP) when desired.

Figure 11:
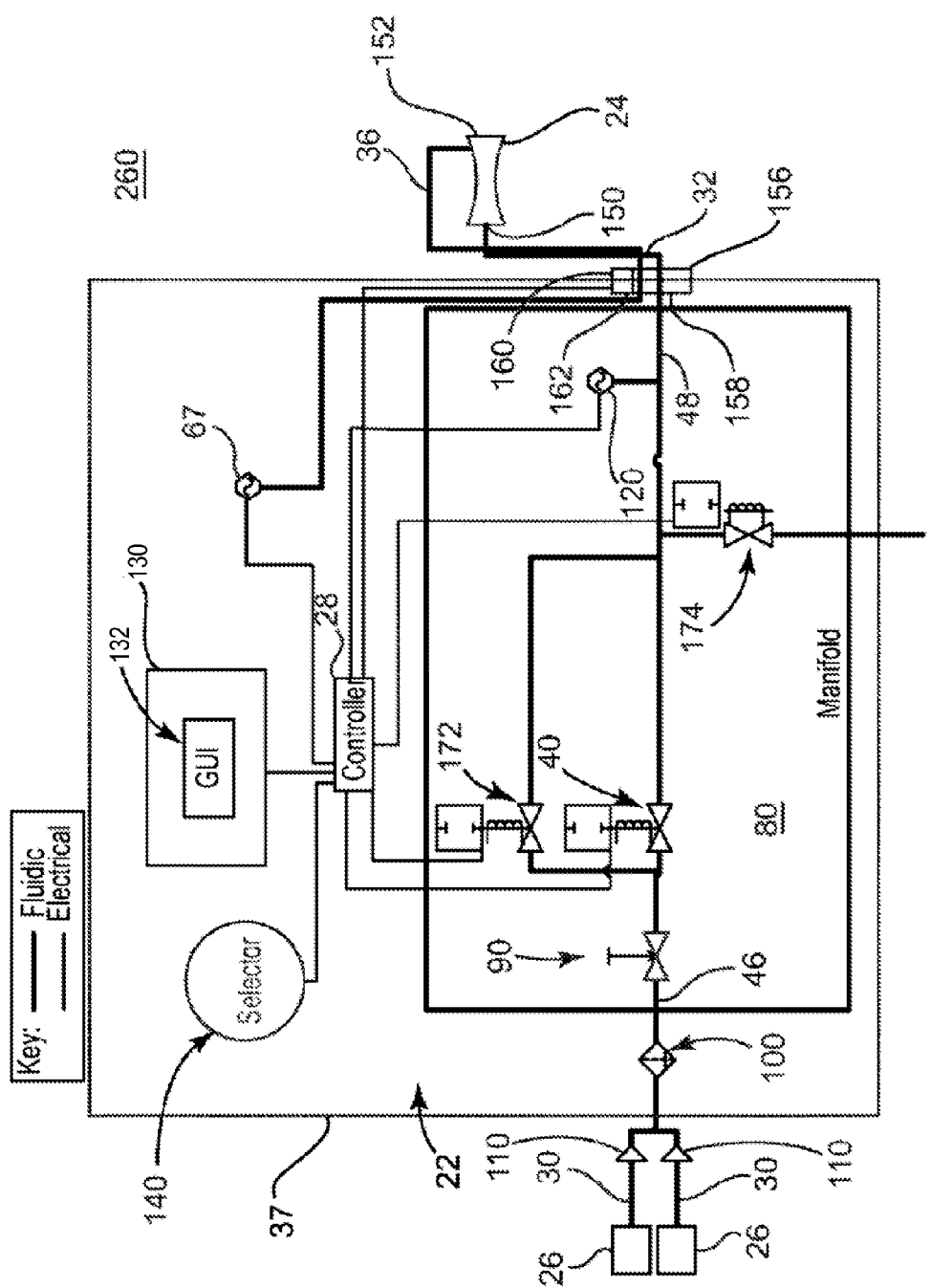

With the alternative respiratory therapy system 260 of FIG. 11, aerosol-related components are removed. Thus, the neb flow valve 70 (FIG. 3) and the corresponding auxiliary line 35 (FIGS. 1 and 3) are eliminated. Although FIG. 11 reflects that the nebulizer 34 (FIG. 3) has also been eliminated, it will be understood that a separate nebulizer unit (not shown) can be separately provided and fluidly connected to the patient interface (though not controlled by the driver unit 22).

Figure 12:
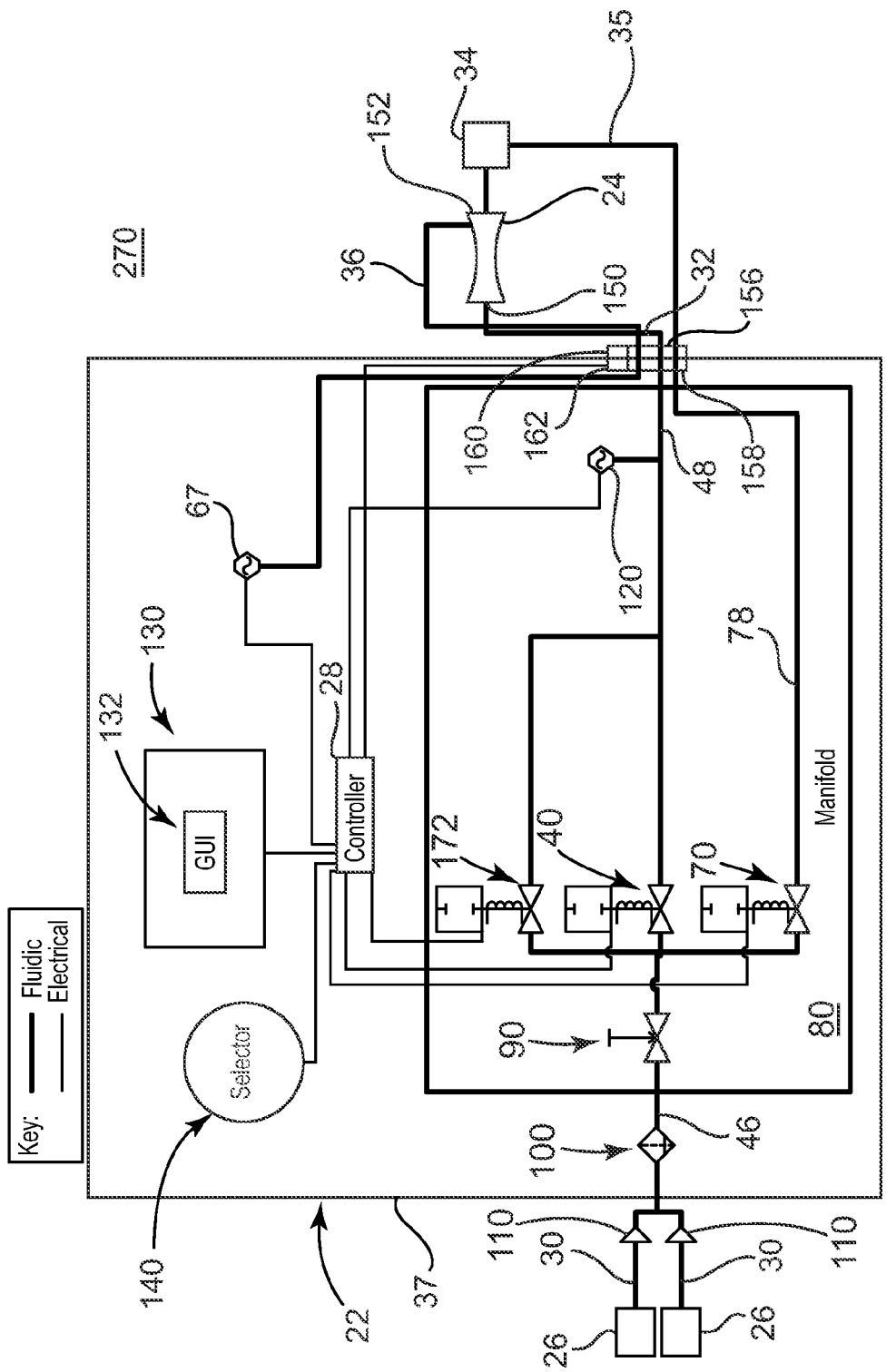

Yet another alternative respiratory therapy system 270 is schematically illustrated in FIG. 12, and again is analogous to the system 170 of FIG. 3. With the respiratory therapy system 270, however, the vent electronic valve 174 (FIG. 3) and related vent line 184 (FIG. 3) is eliminated. Emergency shutoff (under excessive pressure conditions) can be accomplished by the controller 28 operating the electronic valves 40, 172 to their closed state.

Figure 13:
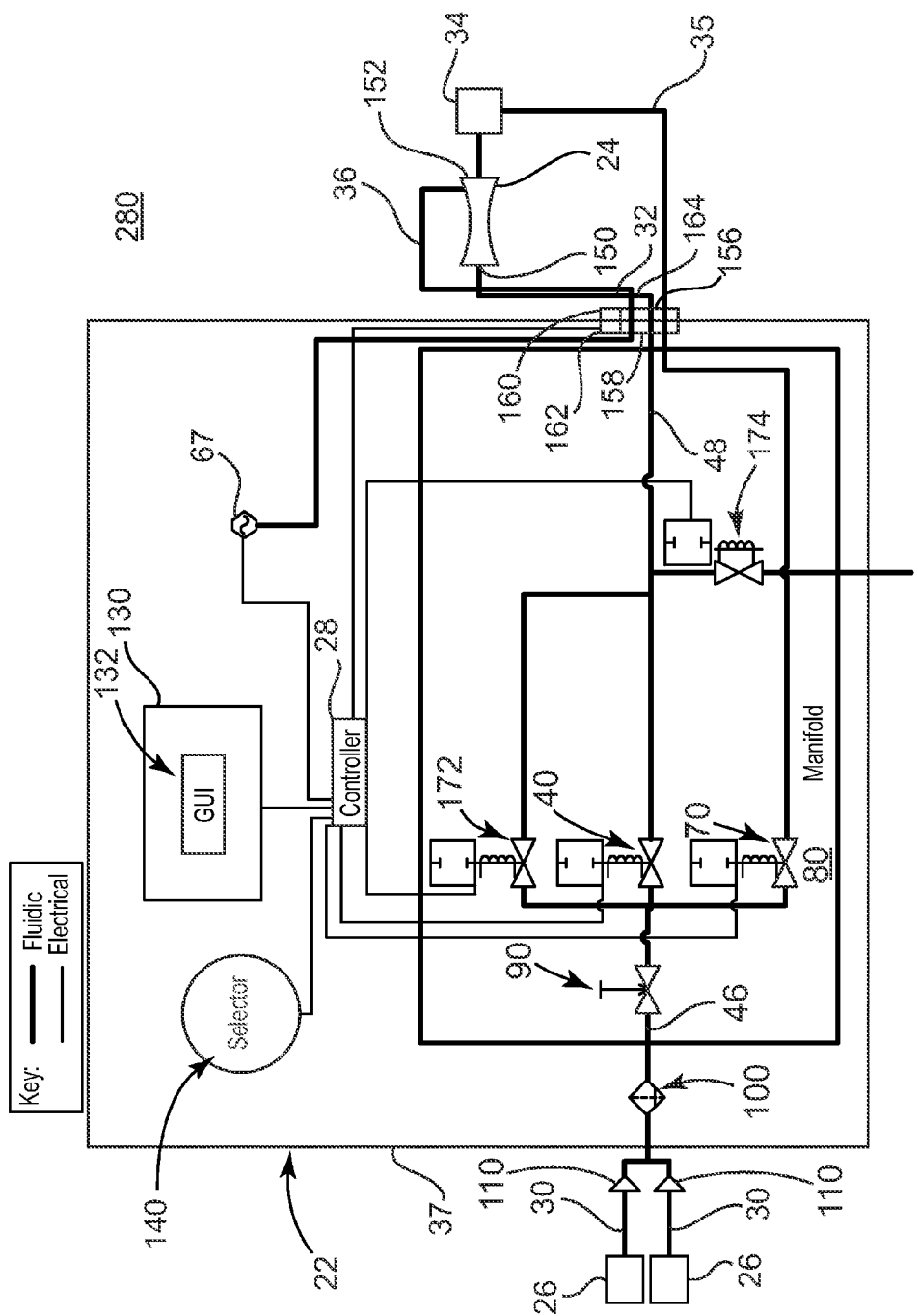

With the alternative respiratory therapy system 280 of FIG. 13, the optional manifold pressure sensor 120 (FIG. 3) is eliminated. Operation of the shutoff electronic valve 174 can be dictated by the controller 28 based upon information from the patient pressure sensor 67 and/or in response to a user-entered command.

Figure 14:
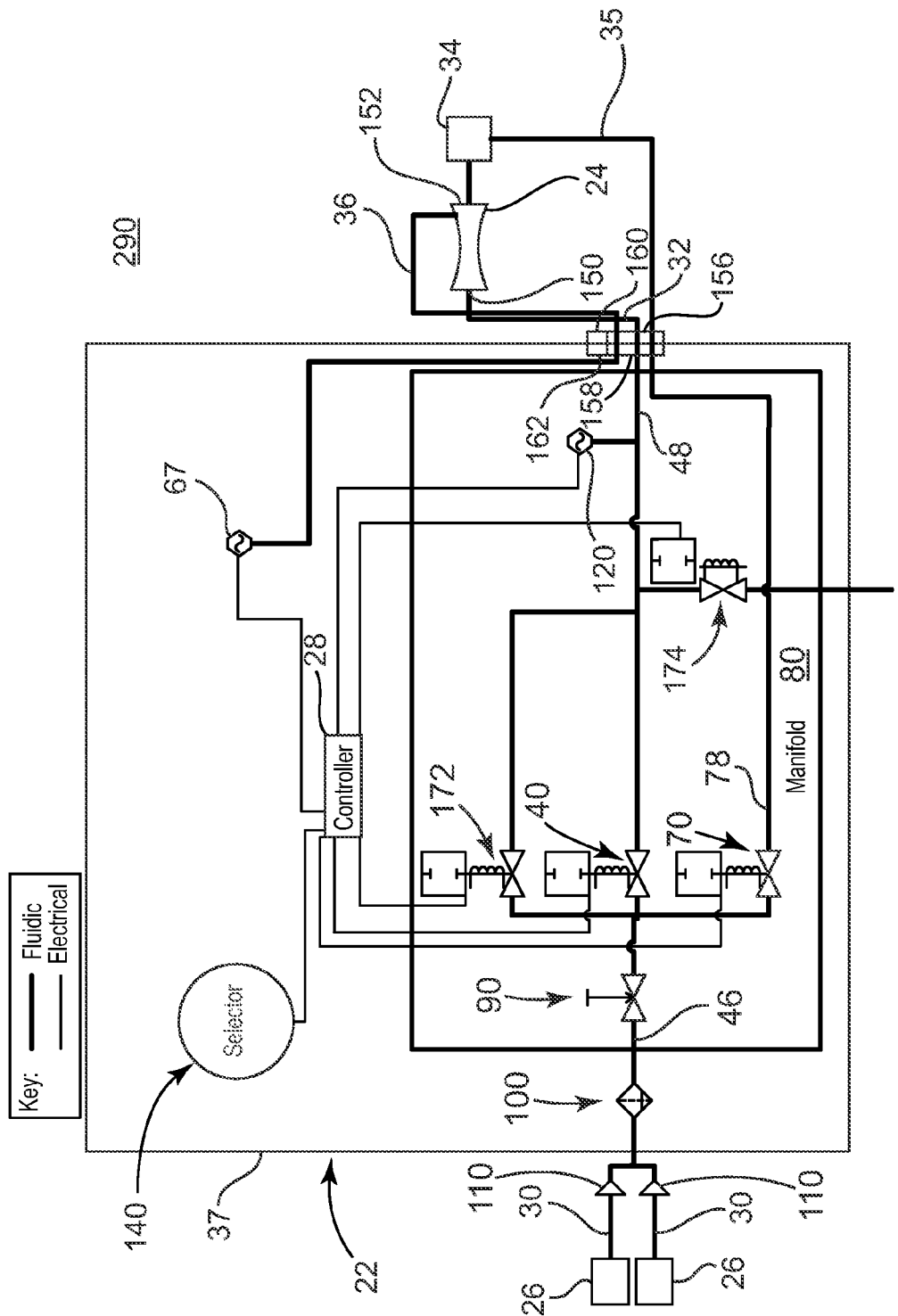

Yet another alternative embodiment respiratory therapy system 290 is schematically shown in FIG. 14. The system 290 is analogous to the system 170 (FIG. 3) previously described, except that the display system 130 (FIG. 3) is eliminated.

As mentioned above, the patient interface device 24 can assume a wide variety of forms that are useful with the driver unit 22. In most general terms, any construction capable of delivering gas flow/pressure to the patient is acceptable. The patient interface device 24 can be disposable, and can include various design features for delivering respiratory therapy. In general terms, the patient interface device 24 defines at least one lumen (e.g., a dual lumen tubing, two or more single lumen tubes, etc.) connected to a handpiece. The flow from the driver unit 22 (via the outlet line 32) travels through one side of the dual lumen tubing (e.g., the inlet end 150) to the handpiece where it is combined with entrained ambient air and delivered to the patient via a mouthpiece or other component such as a mask connected to the outlet end 152. The other side of the dual lumen tubing connects to a pressure port near the patient end of the handpiece. The pressure port, in turn, is adapted for fluid connection to the patient pressure line 36. In one embodiment, a patient pressure sensor can be integrated directly into patient interface device 24, wherein patient interface device 24 would only require a single lumen. In this instance, a means of power to the patient sensor and a means to transmit data to driver unit 22 can be provided to the patient interface device 24. If aerosol therapy is desired, the nebulizer 34 can be fluidly connected to the outlet end 152 of the patient interface device 24, with a mouthpiece connected to an opposite side of the nebulizer via a T-connector and wherein fluid flow from driver unit 22 can be delivered to nebulizer 34 through a separate port via auxiliary line 35.

Additional internal features optionally incorporated with the patient interface device 24 include a venturi or venturi-like assembly (e.g., a movable venturi tube or a stationary venturi tube). Alternatively, the patient interface device 24 can incorporate a non-venturi design, such as a nozzle with a fixed orifice or a nozzle with a mixing throat and no diffuser. The patient interface device 24 may or may not include an entrainment valve or an exhalation valve. Even further, other useful components of the patient interface device 24 can include a dual jet configuration with a basic diverter, configurations adapted to implement a coanda effect, and other designs that do not provide for ambient air entrainment. Once again, any or all of these patient interface device features are optional, and are not required for operation of the system 20 in accordance with the present disclosure.

Figure 15:
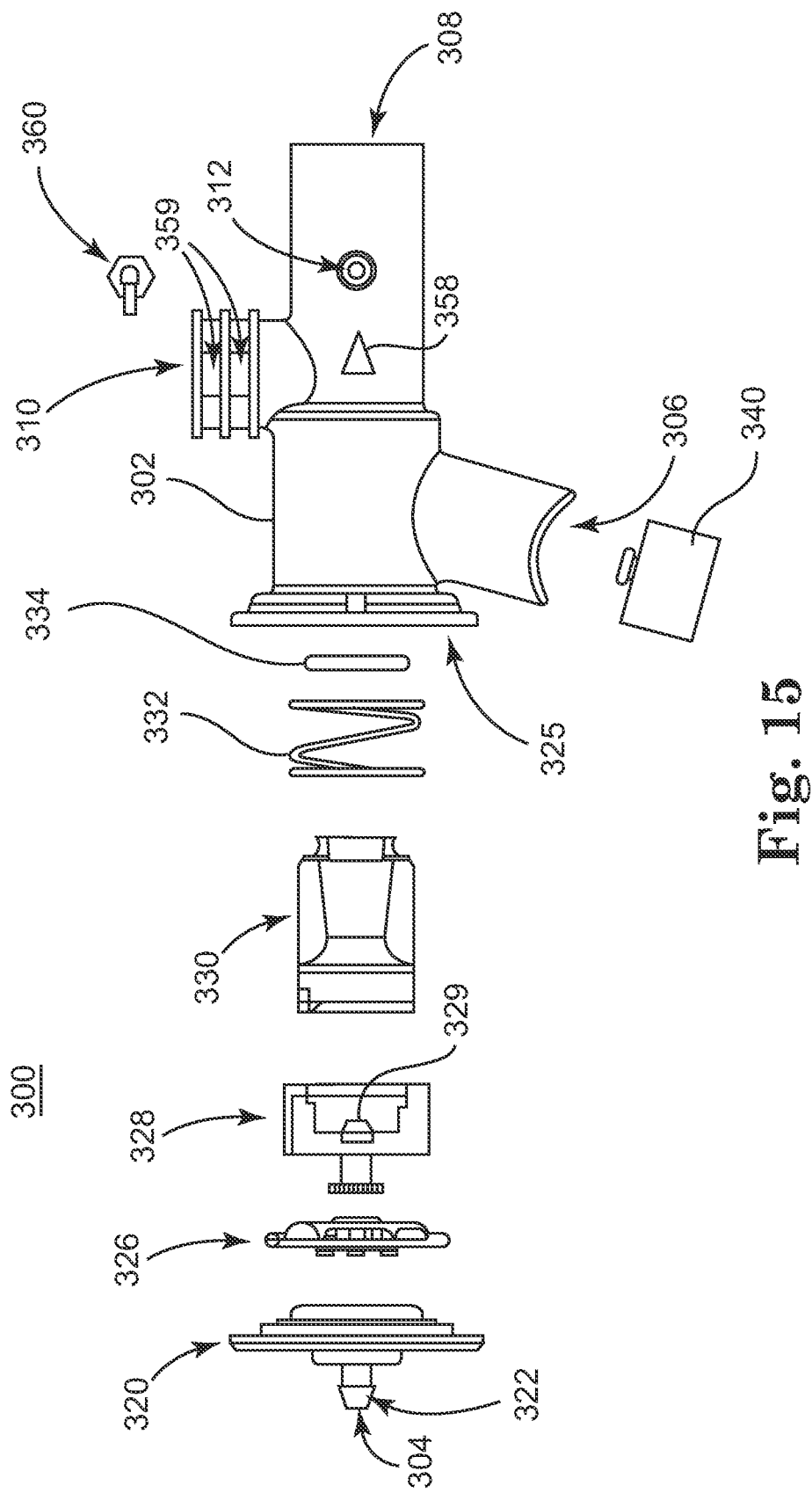
FIGS. 15 and 16 are illustrations of a first embodiment of a patient interface device.
Figure 16:
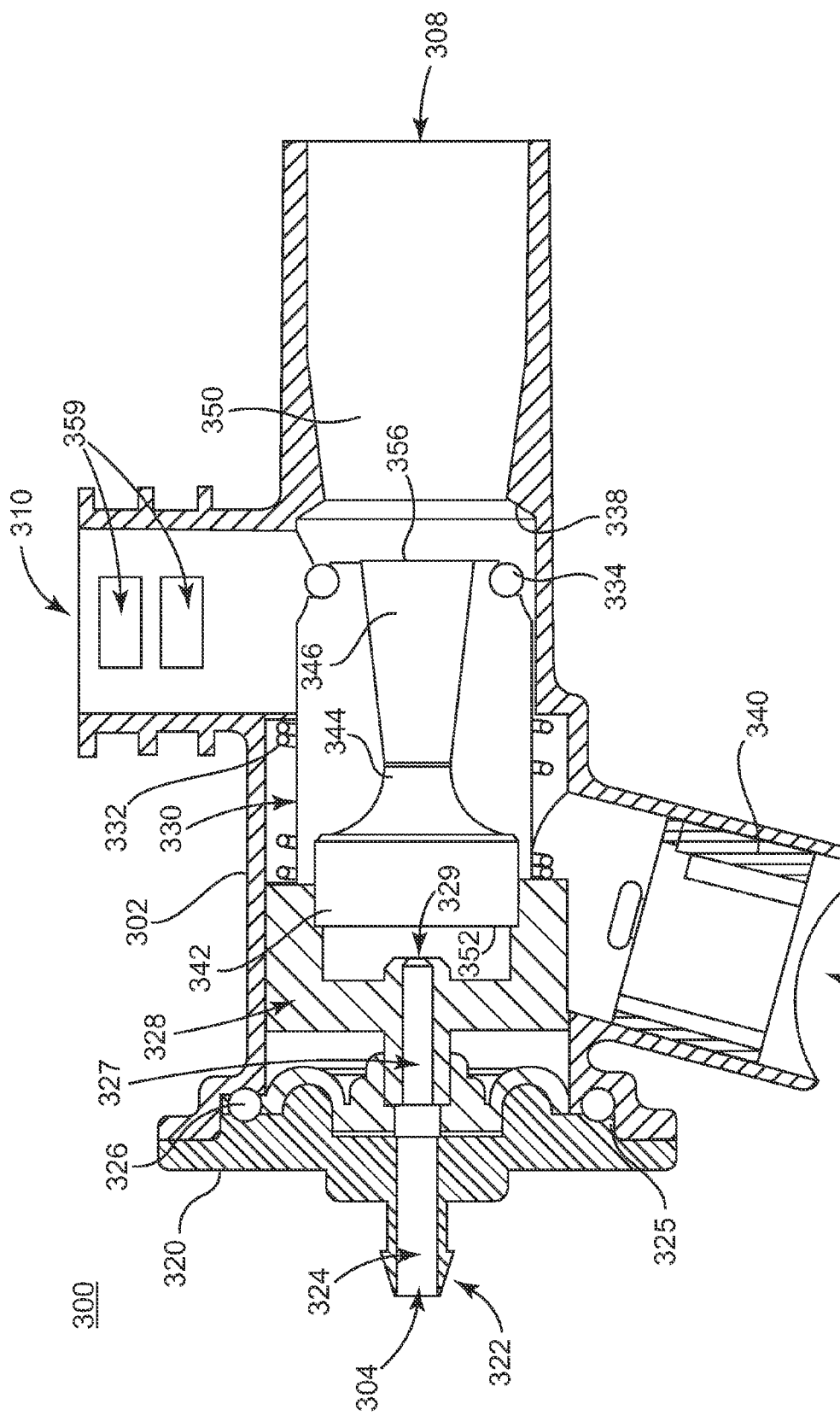

FIGS. 15 and 16 illustrate a first exemplary embodiment of a patient interface device. In particular, FIG. 15 is an exploded view and FIG. 16 is a sectional view of a patient interface device 300. The patient interface device 300 includes a housing 302 and several components disposed within the housing 302. The patient interface device 300 defines several ports, for example, a pulsed air inlet port 304, an entrainment port 306, an outlet connector port 308, an exhaust port 310 and a pressure port 312. Pulsed air enters inlet port 304 from driver 22 (FIG. 1) and ambient air is drawn into housing 302 though entrainment port 306. Air flow is then delivered to outlet connector port 308, which can be configured to couple to a patient mouthpiece or nebulizer. Air exhaled by a patient travels back through outlet connector port 308 and is exhausted through exhaust port 310. Pressure port 312 can be coupled to patient pressure line 36 (FIG. 1) such that pressure in patient interface device 300 can be measured by driver unit 22 (FIG. 1).

In particular, pulsed air enters inlet port 304 through an end cap 320 that includes a connector piece 322 and a central tube 324. End cap 320 is positioned within an internal bore 325 provided in housing 302. Connector piece 322 can be connected to outlet line 32 (FIG. 1). Inlet port 304 is fluidly coupled to central tube 324 to deliver air thereto. A flexible diaphragm 326 establishes a sealed fluid pathway from tube 324 to a corresponding tube 327 of a retainer 328, which terminates at a jet nozzle 329. From nozzle 329, air then enters a venturi assembly 330. Together, retainer 328 and venturi assembly 330 form a jet pump. The jet pump is slidably disposed within housing 302, movable in a back-and-forth manner relative to inlet port 304 and outlet connector port 308. A spring 332 biases the jet pump toward inlet port 304 and away from outlet connector port 308. Additionally, an O-ring 334 is provided to form a seal between venturi assembly 330 and an inner sealing surface 338 of the housing 302. Ambient air can enter housing 302 through a one-way check valve 340 disposed in entrainment port 306. The one-way check valve 340 permits inflow of ambient air into the entrainment port 306, but prevents gas flow out from the entrainment port 306.

With particular reference to FIG. 16, venturi assembly 330 forms an entrainment region 342, a throat region 344 and an expansion region 346 for combining air from inlet port 304 and entrainment port 306 and delivering combined air to a lumen 350 fluidly coupled to outlet connector port 308. In the embodiment illustrated; entrainment region 342 defines an inlet opening 352 to inlet port 304 and entrainment port 306. Throat region 344 defines a tapered, converging portion that routes flow within venturi assembly 330. Expansion region 346 defines a tapered, diverging portion that increases in diameter from the throat region 344 toward lumen 350, terminating at an outlet opening 356. Although other configurations for venturi assembly 330 can be used, in the venturi assembly 330 illustrated in FIGS. 15 and 16, air flow is routed through a converging portion to a diverging portion to lumen 350.

During operation, pulsed gas flow generated by the driver 22 (FIG. 1) enters through inlet port 304. The pulsed air places a force on diaphragm 326, which flexes to impart a force (i.e., a force direction on the throat region in a rightward direction relative to FIG. 16) on the jet pump (i.e. retainer 328 and venturi assembly 330). Pulsed air enters the sliding venturi assembly 330 at the jet nozzle 329. More particularly, airflow from the jet nozzle enters the entrainment region 342 wherein throat region 344 creates a vacuum that in turn draws in ambient air via the entrainment port 306. The combined pulsed and ambient air is directed into the throat region 344. As the force of the flexing diaphragm 326 compresses the spring 332, the sliding jet pump slides or moves toward the outlet connector port 308. Sliding movement continues until a leading end of the venturi assembly 330 (i.e., O-ring 334 carried by the venturi assembly 330) contacts and seals against inner sealing surface 338 of the housing 302. In this sealed position, then, the airflow/pressure pulse is effectively delivered to the outlet connector port 308 and thus the patient. Also, the venturi assembly 330 effectively closes the exhalation port 310 in the sealed position. As the force on the diaphragm 326 is reduced (i.e., at the end of the pressure pulse), the diaphragm 326 and spring 332 force the venturi assembly 330 away from the inner sealing surface 338, opening the pathway between the outlet connector port 308 and the exhalation port 310. Thus, the patient can easily exhale through the outlet connector port 308 and the exhalation port 310 (i.e., the sliding jet pump does not directly resist exhaled airflow from the patient when moved from the sealed position).

In a further embodiment, housing 302 includes a progressive seal 358 (FIG. 15) that is formed of a cut-out section of the housing 302. The progressive seal 358 is tapered to prevent immediate sealing between outlet connector port 308 and ambient (i.e. through exhalation port 310). That is to say, the size of the orifice of the seal 358 decreases as venturi assembly 330 approaches inner sealing surface 338. Thus, sealing between outlet connector port 308 and ambient occurs gradually.

In an alternative embodiment, the exhalation valve can be separate from the venturi assembly. In this case, increased control of the exhalation valve can be provided as well as allowing for a fixed venturi assembly. In still a further embodiment, the exhalation valve can be eliminated.

The outlet connector port 308 can be configured to receive either a patient mouthpiece or a nebulizer (it being understood that the so-connected nebulizer can in turn carry a patient mouthpiece). Connection of the nebulizer (e.g. nebulizer 34 of FIG. 1) is downstream of the venturi assembly 330 and the entrainment port 306. That is to say, flow from the nebulizer via the outlet connector port 308 is not simultaneously entrained into the pulsed air flow with ambient air. Instead, nebulized medication is delivered directly to the patient, carried by the previously-combined pulsed gas flow and entrained ambient air. By locating the nebulizer downstream from the outlet connector port 308, particle knock-down of aerosoled medication within patient interface device 300 is reduced. In particular, medication knock-down within patient interface 300 is prevented, allowing more respirable mass to reach the patient. For example, a percentage of respirable medication (e.g. Albuterol) in mass delivered to a patient can be several times greater (e.g. five times or more) when locating the nebulizer downstream of the connector port, as opposed to directly entraining medication within housing 302.

Exhalation port 310, as illustrated, includes openings 359 to prevent exhalation port 310 from easily being inadvertently sealed, for example by a person's hand or finger. Additionally, a suitable filter (not shown) can be positioned within exhalation port 310 to filter unwanted contaminants from reaching the caregiver. The filter can take various forms such as bacterial, HEPA, viral, etc.

Pressure port 312 can be provided with suitable connection means 360 that connects to patient pressure line 36 (FIG. 1). As discussed above, driver 22 can measure pressure in the patient pressure line 36 through use of pressure sensor 67. The measured pressure can be used to control the one or more valves associated with driver 22. When patient pressure line 36 is purged, fluid exits into lumen 350. Since nebulizer 34 can be located downstream of patient interface device 300, patient pressure line 36 may have increased medicament deposition therein. Thus, purging patient pressure line 36 can be advantageous.

Figure 17:
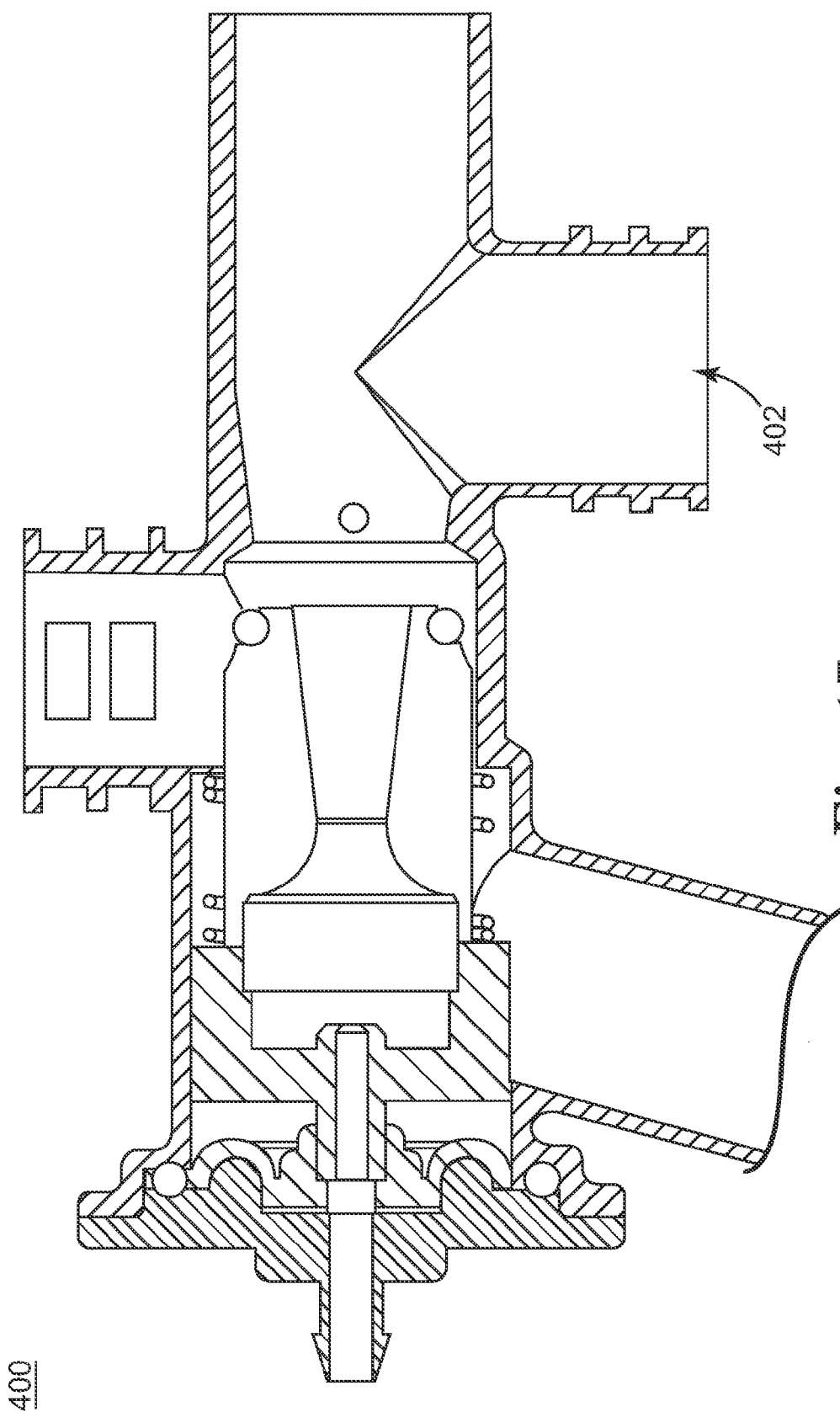
FIG. 17 is an illustration of a second embodiment of a patient interface device.

FIG. 17 illustrates a second exemplary embodiment of a patient interface device 400. The patient interface device 400 includes similar components to the patient interface device 300 illustrated in FIGS. 15 and 16. Additionally, patient interface device 400 includes a nebulizer port 402 directly integrated with outlet connector port 308. In this manner, a nebulizer can be fluidly coupled directly to patient interface device 400 through nebulizer port 402 and downstream from venturi assembly 330. The integrated nebulizer port 402 provides a fixed relation to venturi assembly 330 and a quick setup for a caregiver to insert a compatible nebulizer and reduces dead volume, thereby increasing efficiency of the system.

Figure 18:
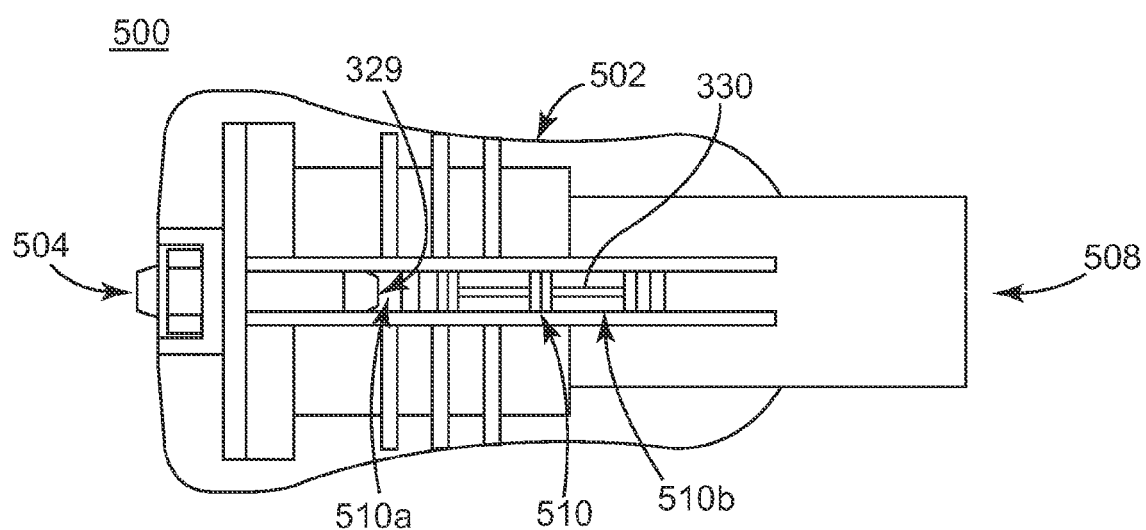
FIGS. 18-20 are illustrations of a third embodiment of a patient interface device.
Figure 19:
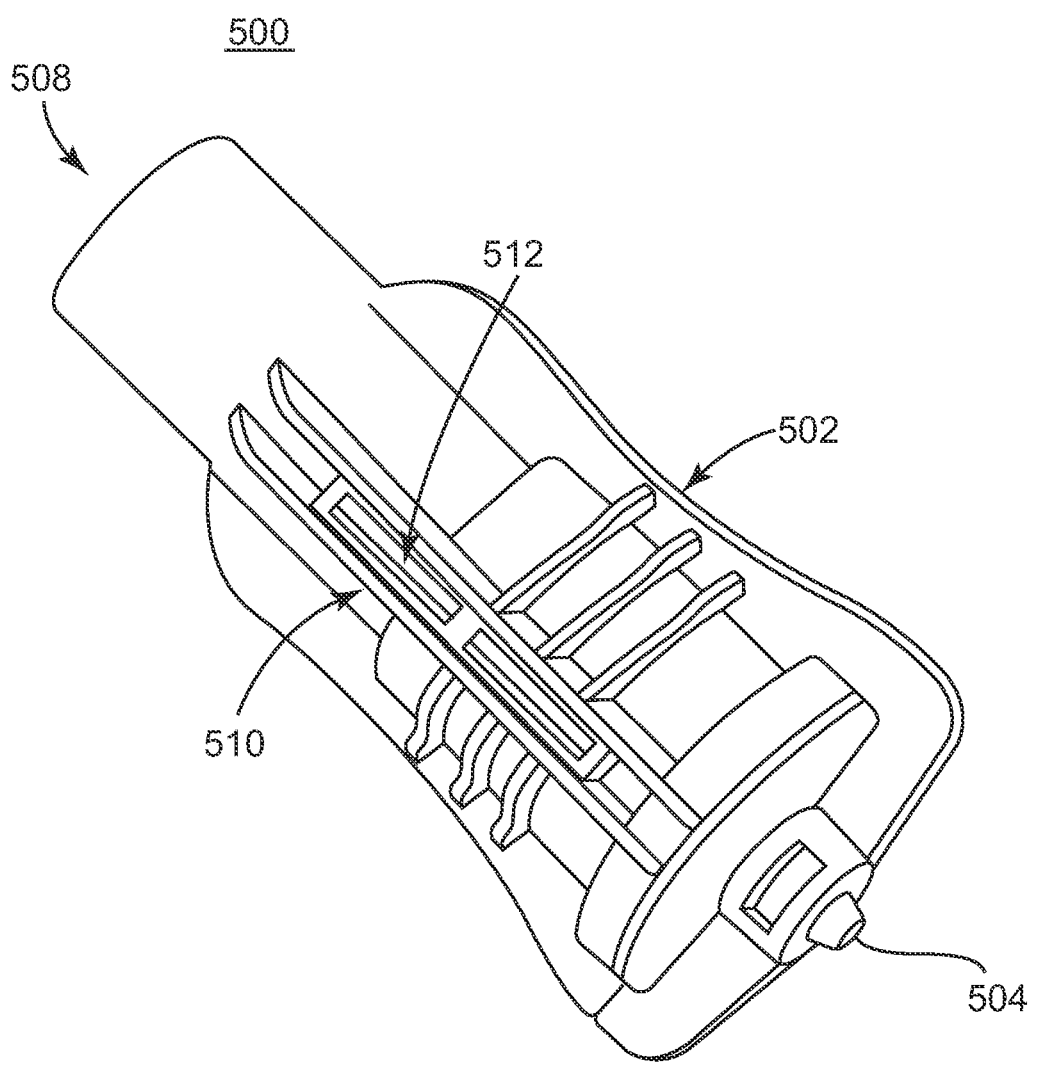
Figure 20:
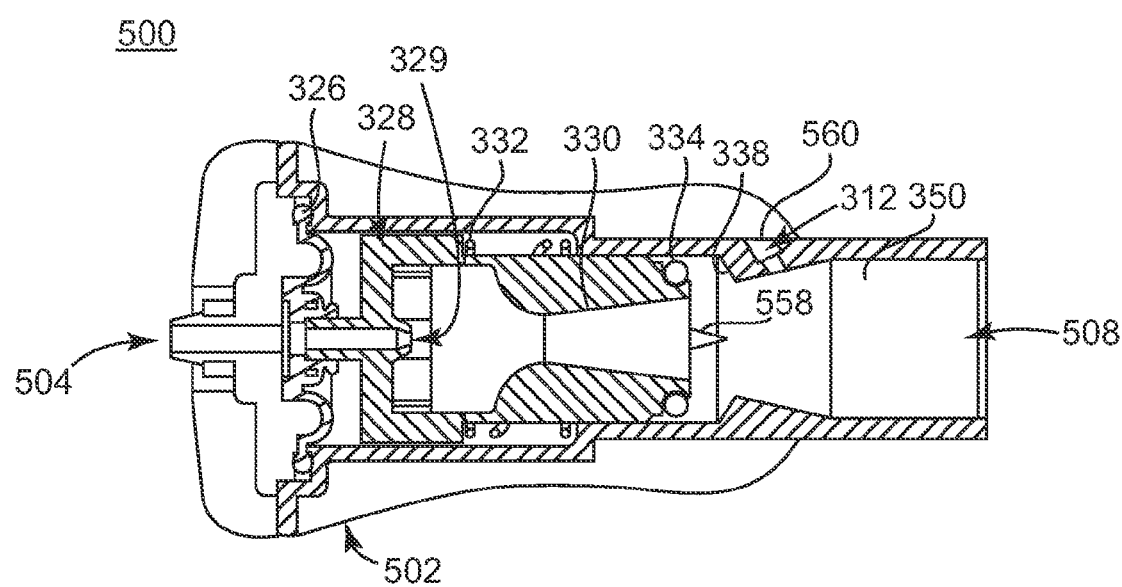

FIGS. 18-20 illustrated a third embodiment of a patient interface device 500. Patient interface device 500 includes several of the same components as patient interface device 300 (FIGS. 15-16) wherein similar components are similarly numbered. As with patient interface device 300, patient interface device 500 includes a housing 502 defining an inlet port 504 and an outlet connector port 508. However, instead of having separate ports for entrainment and exhaust, housing 502 includes a unitary exhaust/entrainment port 510 positioned along a length of the housing 502. During operation, air can be entrained into unitary port 510 through an entrainment portion 510a of unitary port 510 (i.e. upstream of venturi assembly 330) and exhausted through an exhalation portion 510b (i.e. downstream of venturi assembly 330). As illustrated in FIG. 19, if desired, a filter (e.g. bacterial, HEPA, viral) 512 can be positioned within unitary port 510 to prevent unwanted contaminants from entering housing 502.

FIG. 20 is a sectional illustration of patient interface device 500, showing several components disposed within housing 502. Elements within housing 502 operate similarly elements in housing 302 and are illustrated similarly in FIG. 20, for example, pressure port 312, diaphragm 326, retainer 328, nozzle 329, venturi assembly 330, spring 332, O-ring 334, inner sealing surface 338 and lumen 350. In FIG. 20, a progressive seal 558 is cut out of an internal portion of the housing 502. In particular, the progressive seal 558 is formed in inner sealing surface 338 and operates similar to progressive seal 358 of FIG. 15. Also, a connection means 560 is formed integrally with housing 502 and obliquely oriented with respect to an axis coaxial with respect to inlet port 504 and outlet connector port 508.

Figure 21:
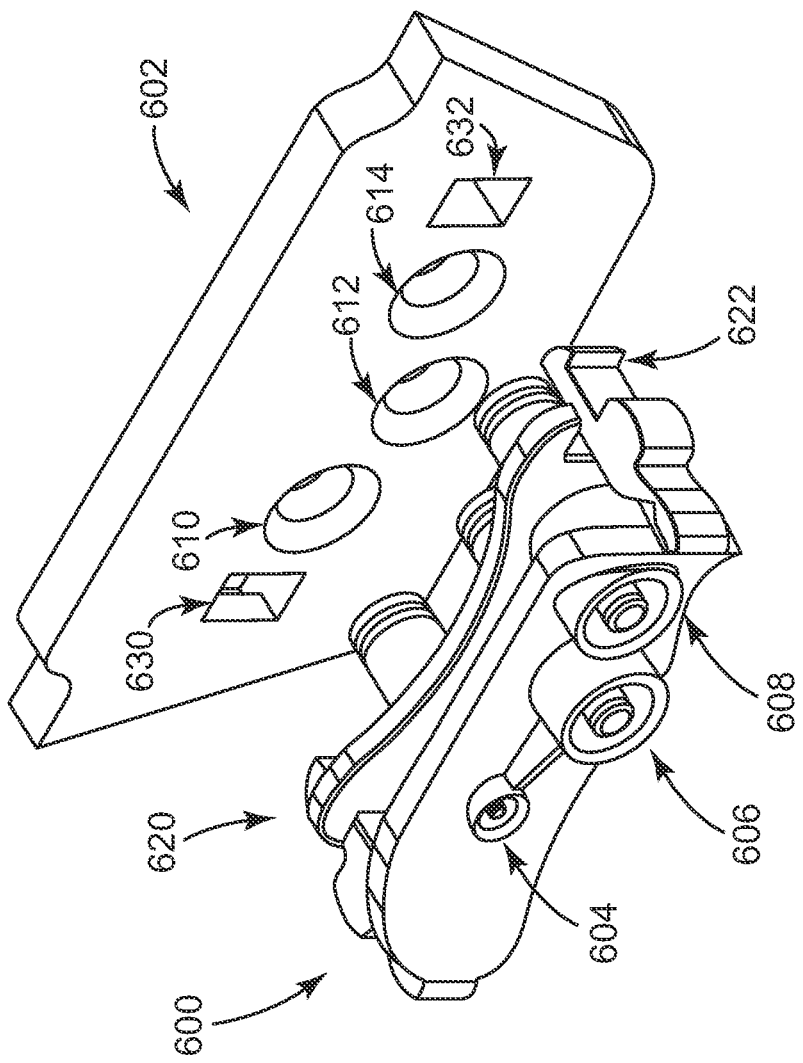
FIG. 21 is an illustration of a connector having multiple ports for fluidly coupling a driver unit to a patient interface device.

FIG. 21 is an illustration of an exemplary connector 600 configured to cooperate with a connector block 602 of a driver unit. Connector 600 can be used to quickly connect a patient interface device to a driver unit. Connector 600 includes ports 604, 606 and 608 that are fluidly connected to corresponding apertures 610, 612 and 614 of connector block 602. Furthermore, ports 604, 606 and 608 can be fluidly coupled to patient pressure line 36, outlet line 32 and auxiliary line 35, respectively. Once lines 32, 35 and 36 are connected to connector 600, ports 604, 606 and 608 can be positioned within apertures 610, 612 and 614. Additionally, connector 600 includes tabs 620 and 622 that cooperate with tab receiving portions 630 and 632, respectively. Tabs 620 and 622 can be resilient members that can be pressed towards each other and inserted into tab receiving portions 630 and 632. Hooks at the end of the tabs 620, 622 can then engage the tab receiving portions 630, 632 such that connector 600 is secured to connector block 602.

Although the present disclosure has been described with respect to preferred embodiments, workers skilled in the art will recognize that changes can be made in form and detail without departing from the spirit and scope of the present disclosure.

What is claimed is:

1. A patient interface assembly for delivering respiratory therapy to a patient, comprising:
 a housing that defines an inlet port and an outlet port, the inlet port being configured to couple to a driver delivering pressurized gas flow to the inlet port;
 a jet pump disposed within the housing and positioned to receive the pressurized gas flow from the inlet port and deliver the pressurized gas flow to the outlet port;
 a nebulizer fluidly coupled to the outlet port to receive the pressurized gas flow therefrom, introduce medication into the pressurized gas flow and deliver medicated gas flow to the patient; and
 a progressive seal positioned in the housing such that, as the jet pump slides toward the outlet port, a gradual seal forms between an exhalation port and the outlet port.

2. The patient interface assembly of claim 1, wherein the housing includes an entrainment port fluidly coupled to receive ambient air and wherein the jet pump is configured to combine the pressurized gas flow from the inlet port and ambient air from the entrainment port.

3. The patient interface assembly of claim 1, wherein the exhalation port is configured to exhaust air from the housing that is received from the patient via the outlet port.

4. The patient interface assembly of claim 3 and further comprising a filter disposed in the exhalation port.

5. The patient interface assembly of claim 1 and further comprising a unitary port fluidly coupling an interior of the housing with ambient air, the unitary port forming an entrainment port fluidly coupling ambient air to the interior of the housing upstream of the jet pump and the exhalation port fluidly coupling ambient air to the interior of the housing downstream of the jet pump.

6. The patient interface assembly of claim 1, wherein the jet pump includes a venturi assembly defining an entrainment region, a throat region and an expansion region.

7. The patient interface assembly of claim 1, wherein the jet pump is slidable within the housing in a direction relative to the inlet port and the outlet port.

8. The patient interface assembly of claim 7, and further comprising a spring positioned within the housing to bias the jet pump toward the inlet port.

9. The patient interface assembly of claim 7, and further comprising a diaphragm configured to deflect in response to pressurized gas flow delivered to the inlet port so as to force the jet pump in a direction toward the outlet port.

10. The patient interface assembly of claim 7, wherein the exhalation port is configured to exhaust air from the housing.

11. The patient interface assembly of claim 1, wherein the housing includes a nebulizer port to fluidly couple the nebulizer to the housing.

12. The patient interface assembly of claim 1, wherein the progressive seal comprises a cut out through the housing that tapers toward the outlet port.

13. A system for delivering respiratory therapy to a patient, comprising:
 a driver unit configured to deliver pressurized gas flow;
 a patient interface device fluidly coupled to the driver unit and including an inlet port, an outlet port and a jet pump positioned between the inlet port and the outlet port, wherein the inlet port is positioned to receive the pressurized gas flow from the driver unit and the jet pump is positioned to receive gas flow from the inlet port and deliver gas flow to the outlet port;
 a nebulizer fluidly coupled to the outlet port to receive the pressurized gas flow therefrom, introduce medication into the pressurized gas flow and deliver medicated gas flow to the patient; and
 a progressive seal positioned in the patient interface device such that, as the jet pump moves toward the outlet port, a gradual seal forms between an exhalation port and the outlet port.

14. The system of claim 13, wherein the patient interface device defines an entrainment port, wherein the jet pump is configured to combine pressurized gas from the inlet port and ambient air from the entrainment port to deliver combined gas flow to the outlet port and wherein the exhalation port is configured to exhaust air from the patient interface device received from the patient.

15. The system of claim 13, wherein the jet pump includes a venturi assembly defining an entrainment region, a throat region and an expansion region.

16. The system of claim 13, wherein the patient interface device includes a housing and wherein the jet pump is slidable within the housing in a direction relative to the inlet port and the outlet port.

17. The system of claim 16, wherein the housing further includes a spring adapted to bias the jet pump towards the inlet port.

18. The system of claim 16, wherein the housing includes a nebulizer port to fluidly couple the nebulizer to the housing.

19. The system of claim 13, wherein a patient pressure line is fluidly coupled to the driver unit and the patient interface device between the jet pump and outlet port.

20. The system of claim 13, wherein the progressive seal is positioned on an internal surface of the patient interface device and comprises a cut out that tapers toward the outlet port.

* * * * *